(12) United States Patent
Pearson et al.

(10) Patent No.: US 11,377,416 B2
(45) Date of Patent: Jul. 5, 2022

(54) CRYSTALLINE FORMS OF HYDROXYNORKETAMINE

(71) Applicant: SMALL PHARMA LTD, London (GB)

(72) Inventors: David Pearson, Penicuik (GB); Lorraine Sharp, Penicuik (GB); Alan Armstrong, London (GB); Richard Myerson, Derbyshire (GB); Jonathan Hull, Derbyshire (GB); Paul Blaney, Derbyshire (GB); Peter Rands, London (GB); Marie Layzell, London (GB); Zelah Joel, London (GB)

(73) Assignee: SMALL PHARMA LTD., London (GB)

( * ) Notice: Subject to any disclaimer, the term of this patent is extended or adjusted under 35 U.S.C. 154(b) by 0 days.

(21) Appl. No.: 16/635,406

(22) PCT Filed: Jul. 31, 2018

(86) PCT No.: PCT/GB2018/052193
§ 371 (c)(1),
(2) Date: Jan. 30, 2020

(87) PCT Pub. No.: WO2019/025792
PCT Pub. Date: Feb. 7, 2019

(65) Prior Publication Data
US 2020/0157040 A1 May 21, 2020

(30) Foreign Application Priority Data
Jul. 31, 2017 (GB) .................................. 1712304
Sep. 18, 2017 (GB) .................................. 1715010
Sep. 25, 2017 (GB) .................................. 1715500

(51) Int. Cl.
*C07C 225/20* (2006.01)
*A61K 9/20* (2006.01)
*A61K 9/48* (2006.01)

(52) U.S. Cl.
CPC .......... *C07C 225/20* (2013.01); *A61K 9/2054* (2013.01); *A61K 9/4825* (2013.01); *C07B 2200/13* (2013.01); *C07C 2601/14* (2017.05)

(58) Field of Classification Search
None
See application file for complete search history.

(56) References Cited

U.S. PATENT DOCUMENTS 5,817,699 A 10/1998 Flores et al.
2004/0158075 A1* 8/2004 Youn .................. A61P 9/10
546/315

(Continued)

FOREIGN PATENT DOCUMENTS

EP 2766339 B1 6/2021
WO WO 2013-056229 A1 4/2013

(Continued)

OTHER PUBLICATIONS

Yixin Han et al., Simple Enantioselective Synthesis of Hydroxynorketamine and Related Potential Rapid-Onset, Oct. 6, 2017.

(Continued)

*Primary Examiner* — Sudhakar Katakam
*Assistant Examiner* — Jennifer C Sawyer
(74) *Attorney, Agent, or Firm* — Heslin Rothenberg Farley & Mesiti P.C.

(57) ABSTRACT

The present invention provides novel, stable, processable and pharmaceutically acceptable salt forms of 2R,6R-hydroxynorketamine or 2S,6S-hydroxynorketamine with high aqueous solubility.

4 Claims, 9 Drawing Sheets

(56) References Cited

U.S. PATENT DOCUMENTS

| | | | |
|---|---|---|---|
| 2014/0079740 | A1 | 3/2014 | Salama |
| 2015/0196501 | A1 | 7/2015 | Erickson et al. |
| 2016/0368884 | A1* | 12/2016 | de Diego ............. A61P 25/22 |
| 2018/0098993 | A1* | 4/2018 | Wainer ............. A61P 25/04 |
| 2018/0289637 | A1 | 10/2018 | Laufer et al. |
| 2019/0240184 | A1 | 8/2019 | Hashimoto et al. |
| 2019/0380978 | A1 | 12/2019 | Rands et al. |
| 2021/0315840 | A1 | 10/2021 | Robbins et al. |

FOREIGN PATENT DOCUMENTS

| | | |
|---|---|---|
| WO | WO 2014/020155 A1 | 6/2014 |
| WO | WO 2014-117089 A1 | 7/2014 |
| WO | WO 2016-073653 A1 | 5/2016 |
| WO | WO 2016-186968 A1 | 11/2016 |
| WO | WO 2017-087388 A1 | 5/2017 |
| WO | WO 2017-087691 A1 | 5/2017 |
| WO | WO 2017-208031 A1 | 12/2017 |
| WO | WO 2018-053221 A1 | 3/2018 |
| WO | WO 2018-079693 A1 | 5/2018 |
| WO | WO 2018-102488 A1 | 6/2018 |

OTHER PUBLICATIONS

Nagendra S. Singh et al., "Ketamine Metabolites Enantioselectively Decrease Intracellular D-Serine Concentrations in PC-12 Cells", Apr. 20, 2016.

Hayley et al., Neurocognitive and behavioural performance of healthy volunteers receiving an increasing analgesic-range infusion of ketamine, Psychopharmacology, Feb. 23, 2018.

Colonna, et al., "A randomized, double-blind, 24-week study of escitalopram versus citalopram in primary care patients with major depressive disorder", 2005, 11 pages.

Panos Zanos, et al., "NMDAR Inhibition-Independent Antidepressant Actions of Ketamine Metabolites", Nature, May 26, 2016, 33 pages.

Leung et al., "Comparative Pharmacology in the Rat of Ketamine and Its Two Principal Metabolites, Norketamine and (Z)-6-Hydroxynorketamine", Journal of Medicinal Chemistry, vol. 29, No. 11, Oct. 28, 1986, 4 pages.

Woolf et al, "Synthesis of (Z)- and (E)-hydroxyketamine", Journal of Organic Chemistry, vol. 49, No. 18, Feb. 6, 1984, 6 pages.

Stevens et al, "Amino Ketone Rearrangements.", Journal of Organic Chemistry, vol. 31, No. 8, Mar. 14, 1966, 7 pages.

Hashiyama et al, "alpha-Hydroxy Ketones in High Enantiomeric Purity from Asymmetric Dihydroxylation of Enol Ethers", Journal of Organic Chemistry, vol. 57, No. 19, Jun. 11, 1992, 2 pages.

Roth et al. "The Ketamine Analogue Methoxetamine and 3- and 4-Methoxy Analogues of Phencyclidine are High Affinity and Selective Ligands for the Glutamate NMDA Receptor", Plos One (Online), vol. 8, No. 3, 5 pages. Mar. 2013.

Zanda et al. "Methoxetamine affects brain processing involved in emotional response in rats", British Journal of Pharmacology, vol. 174, 13 pages Jul. 6, 2017.

Wood et al. "Acute toxicity associated with the recreational use of the ketamine derivative methoxetamine" European Journal of Clinical Pharmacology, vol. 68, 4 pages. Dec. 29, 2011.

Menzies et al. "Characterizing metabolites and potential metabolic pathways for the novel psychoactive substance methoxetamine", Drug Testing and Analysis, vol. 6, 11 pages. 2014.

Obrect, et al., "Eine neue lacton synthese via 2-oxazolin-5-one als zwischenprodukte", vol. 25, 8 pages (Abstract in English) Jan. 1984.

* cited by examiner

CRYSTALLINE FORMS OF HYDROXYNORKETAMINE

CROSS-REFERENCE TO RELATED APPLICATIONS

This application is the National Stage Entry under 35 U.S.C. § 371 Patent Cooperation Treaty Application No. PCT/GB2018/052193, filed Jul. 31, 2018, which claims the benefit of Great Britain Application No. 1712304.3 filed Jul. 31, 2017, and Great Britain Application No. 1715010.3 filed Sep. 18, 2017, and Great Britain Application No. 1715500.3 filed Sep. 25, 2017, which is incorporated herein by reference as if fully set forth.

FIELD OF THE INVENTION

The present invention provides novel, stable, processable and pharmaceutically acceptable salt forms of 2R,6R-hydroxynorketamine or 2S,6S-hydroxynorketamine with high aqueous solubility.

BACKGROUND OF THE INVENTION

Ketamine derivatives, and in particular compounds derived from the ketamine metabolite 2R,6R-hydroxynorketamine and 2S,6S-hydroxynorketamine, show promise as antidepressant agents.

Parenteral formulations of 2R,6R-hydroxynorketamine and 2S,6S-hydroxynorketamine are known from Zanos et al, Nature, (2016), 533, 481-486. However, parenteral formulations suffer drawbacks in the treatment of most depression sufferers, for whom treatment in an outpatient setting without the need of a medical professional would be preferable. The provision of solid oral dosage forms of 2R,6R-hydroxynorketamine and 2S,6S-hydroxynorketamine is therefore advantageous to parenteral dosage forms. There are, however, challenges in the development of solid oral dosage forms of 2R,6R-hydroxynorketamine and 2S,6S-hydroxynorketamine. For example, both compounds in the free base form readily form a viscous oil or gum under ambient conditions, are chemically unstable with a tendency to dimerise, and are particularly difficult to process into a pharmaceutical formulation unless in the liquid state.

SUMMARY OF THE INVENTION

A first aspect of the present invention provides an acid addition salt of 2R,6R-hydroxynorketamine or 2S,6S-hydroxynorketamine obtainable by reaction with an organic acid comprising either (i) two or more carboxylic acid groups, or (ii) one or more carboxylic acid groups and an amide group.

In embodiments of all aspects of the present invention, the acid addition salt is not 2R,6R-hydroxynorketamine L-tartrate or 2S,6S-hydroxynorketamine D-tartrate.

In preferred embodiments of the first aspect the organic acid has Formula I or II

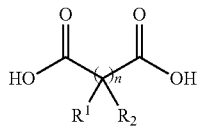

I

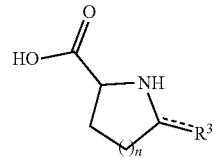

II wherein n=0-3,
R$^1$ and R$^2$ are each independently selected from —H, —OH, and —COOH, and wherein when n=2 or 3, two adjacent R$^2$ groups may together represent a C═C bond, and wherein
R$^3$ is —H, —OH, ═O, or —COOH.

It has been discovered that 2R,6R-hydroxynorketamine and 2S,6S-hydroxynorketamine form crystalline salts readily with organic acids as described herein. Organic acids as used in the present invention may be chiral, enabling the formation of a pharmaceutically acceptable salt to be performed simultaneously with chiral resolution of the active agent. Moreover, crystalline salts of the present invention display unexpectedly high aqueous solubility. Advantages conferred by the high solubility of the acid addition salts of the present invention include high oral bioavailability, which enables optimised solid oral dosage forms to achieve concentrations of systemic circulation necessary to maximise the pharmacological response to 2R,6R-hydroxynorketamine and 2S,6S-hydroxynorketamine.

In embodiments of the present invention, the acid addition salt is obtainable with a chiral organic acid having Formula III, IV or V:

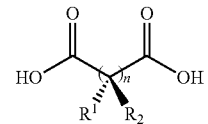

III

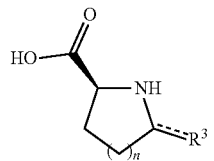

IV

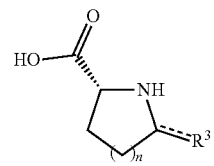

V wherein n=0-3,
R$^1$ and R$^2$ are each independently selected from —H, —OH, and —COOH, wherein at least one pair of R$^1$ and R$^2$ are different, and wherein when n=2 or 3, two adjacent R$^2$ groups may together represent a C═C bond, and wherein
R$^3$ is —H, —OH, ═O, or —COOH.

In embodiments of the invention the acid addition salt is obtainable with an organic acid of Formula I, wherein n=1 or 2, and wherein each R$^1$ is H, one or both R$^2$ is —OH and any remaining R$^2$ is —H.

In embodiments of the invention the acid addition salt is obtainable with an organic acid of Formula I, wherein n=2 or 3, and wherein each $R^1$ is H, two adjacent $R^2$ groups are taken together to represent a C=C bond, and any remaining $R^2$ is —H.

In embodiments of the invention the acid addition salt is obtainable with an organic acid of Formula I, wherein n=2, and wherein each $R^1$ is —H and both $R^2$ groups are taken together to represent a C=C bond.

In embodiments of the invention the acid addition salt is obtainable by reaction with an organic acid of Formula II, wherein n=1 or 2, and wherein $R^3$ is =O.

In preferred embodiments of the first aspect of the present invention, the acid addition salt is selected from aspartic acid, citric acid, fumaric acid, glutaric acid, glutamic acid, hippuric acid, malic acid, maleic acid, mucic acid, oxalic acid, pyroglutamic acid, and succinic acid.

In preferred embodiments of the first aspect of the present invention, the acid addition salt is selected from citric acid, L-malic acid, D-malic acid, fumaric acid, D-pyroglutamic acid, and L-pyroglutamic acid.

In preferred embodiments of the first aspect the organic acid is homochiral.

In preferred embodiments of the first aspect of the present invention, the acid addition salt is selected from 2R,6R-hydroxynorketamine difumarate, 2S,6S-hydroxynorketamine difumarate, 2S,6S-hydroxynorketamine D-pyroglutamate, 2R, 6R-hydroxynorketamine L-pyroglutamate, 2R,6R-hydroxynorketamine L-malate, and 2S,6S-hydroxynorketamine D-malate.

In preferred embodiments of the first aspect of the present invention, the acid addition salt is in substantially crystalline form.

A second aspect of the present invention provides a crystalline acid addition salt of 2R,6R-hydroxynorketamine or 2S,6S-hydroxynorketamine having an X-ray powder diffraction pattern comprising characteristic peaks expressed in degrees 2-theta at positions 19.2, 26.4 and 31.5.

In preferred embodiments of the second aspect the crystalline acid addition salt of 2R,6R-hydroxynorketamine or 2S,6S-hydroxynorketamine having an X-ray powder diffraction pattern further comprising characteristic peaks expressed in degrees 2-theta at positions 14.1, 16.9, 23.5, 24.0 and 29.9.

In preferred embodiments of the second aspect the acid addition salt is obtainable according to the first aspect of the present invention.

In embodiments the acid addition salt is selected from 2R,6R-hydroxynorketamine L-tartrate and 2S,6S-hydroxynorketamine D-tartrate and displays an X-ray powder diffraction pattern comprising characteristic peaks expressed in degrees 2-theta at positions 22.7, 25.7 and 28.7.

In embodiments the acid addition salt is selected from 2R,6R-hydroxynorketamine L-tartrate and 2S,6S-hydroxynorketamine D-tartrate and displays an X-ray powder diffraction pattern further comprising characteristic peaks expressed in degrees 2-theta at positions 6.5 and 12.8.

In embodiments the acid addition salt is selected from 2R,6R-hydroxynorketamine L-tartrate and 2S,6S-hydroxynorketamine D-tartrate and displays an X-ray powder diffraction pattern further comprising characteristic peaks expressed in degrees 2-theta at positions 10.2, 17.2, 20.3, 21.2, 21.9 and 30.5, and wherein the acid addition salt is anhydrous. In embodiments the anhydrous 2R,6R-hydroxynorketamine L-tartrate or 2S,6S-hydroxynorketamine D-tartrate has an X-ray powder diffraction pattern further comprising characteristic peaks expressed in degrees 2-theta at positions 11.4, 13.8, 16.2, 26.5, 26.7, 29.5, 31.3 and 32.6.

In embodiments the acid addition salt is selected from 2R,6R-hydroxynorketamine L-tartrate and 2S,6S-hydroxynorketamine D-tartrate and displays an X-ray powder diffraction pattern further comprising characteristic peaks expressed in degrees 2-theta at positions 8.8, 17.6, 23.7, 25.5, 25.6, 28.4 and 30.9, and wherein the acid addition salt is hydrated. In embodiments the anhydrous 2R,6R-hydroxynorketamine L-tartrate or 2S,6S-hydroxynorketamine D-tartrate has an X-ray powder diffraction pattern further comprising characteristic peaks expressed in degrees 2-theta at positions 13.7, 15.0, 18.6, 19.8, 21.4, 23.2, 29.2, 32.2 and 34.5.

In embodiments the acid addition salt is selected from 2R,6R-hydroxynorketamine difumarate and 2S,6S-hydroxynorketamine difumarate and displays an X-ray powder diffraction pattern comprising characteristic peaks expressed in degrees 2-theta at positions 11.7, 12.4, 22.5 and 22.8.

In embodiments the acid addition salt is selected from 2R,6R-hydroxynorketamine difumarate and 2S,6S-hydroxynorketamine difumarate and displays an X-ray powder diffraction pattern further comprising characteristic peaks expressed in degrees 2-theta at positions 14.7, 16.5, 18.8, 26.8 and 29.4.

In embodiments the acid addition salt is selected from 2R,6R-hydroxynorketamine difumarate and 2S,6S-hydroxynorketamine difumarate and displays an X-ray powder diffraction pattern further comprising characteristic peaks expressed in degrees 2-theta at positions 10.2, 21.4, 23.2, 25.7, and 29.7.

In embodiments the acid addition salt is selected from 2R,6R-hydroxynorketamine difumarate and 2S,6S-hydroxynorketamine difumarate and displays an X-ray powder diffraction pattern further comprising characteristic peaks expressed in degrees 2-theta at positions 18.3, 20.4, 31.0 and 33.0.

In embodiments the acid addition salt is selected from 2R,6R-hydroxynorketamine L-malate and 2S,6S-hydroxynorketamine D-malate and displays an X-ray powder diffraction pattern comprising a characteristic peak expressed in degrees 2-theta at position 23.1.

In embodiments the acid addition salt is selected from 2R,6R-hydroxynorketamine L-pyroglutamate and 2S,6S-hydroxynorketamine D-pyroglutamate having an X-ray powder diffraction pattern comprising characteristic peaks expressed in degrees 2-theta at position 14.3.

In embodiments the acid addition salt is selected from 2R,6R-hydroxynorketamine L-pyroglutamate and 2S,6S-hydroxynorketamine D-pyroglutamate having an X-ray powder diffraction pattern further comprising characteristic peaks expressed in degrees 2-theta at positions 19.9 and 23.8.

In embodiments the acid addition salt is selected from 2R,6R-hydroxynorketamine L-pyroglutamate and 2S,6S-hydroxynorketamine D-pyroglutamate having an X-ray powder diffraction pattern further comprising characteristic peaks expressed in degrees 2-theta at positions 12.0, 13.6, 15.2, 20.8, 26.2, and 28.9.

In embodiments the acid addition salt is selected from 2R,6R-hydroxynorketamine L-pyroglutamate and 2S,6S-hydroxynorketamine D-pyroglutamate having an X-ray powder diffraction pattern further comprising characteristic peaks expressed in degrees 2-theta at positions 12.8, 17.6, 18.1, and 25.5.

In embodiments the acid addition salt is selected from 2R,6R-hydroxynorketamine L-pyroglutamate and 2S,6S- hydroxynorketamine D-pyroglutamate having an X-ray powder diffraction pattern further comprising characteristic peaks expressed in degrees 2-theta at positions 13.8, 14.1, 17.8, 20.3, 21.0, 21.8, 22.7, 24.6, 25.0, 25.3, 27.3, 28.5, 28.7, 30.6, 32.3, 32.7, 33.3, 33.9, and 34.1.

In embodiments the acid addition salt is selected from 2R,6R-hydroxynorketamine L-pyroglutamate and 2S,6S-hydroxynorketamine D-pyroglutamate having an X-ray powder diffraction pattern further comprising characteristic peaks expressed in degrees 2-theta at positions 9.0, 16.6, 21.4, 22.4, 23.1, 25.7, 26.5, 27.8, 28.2, 29.3, 30.1, 31.1, 31.5, 33.1, 33.7, and 34.6.

In embodiments the acid addition salt is obtained by precipitation or crystallisation from an organic solvent, for example acetonitrile, isopropyl acetate, t-butyl methyl ether, ethyl acetate, or diisopropyl ether. A third embodiment of the present invention provides a dosage form comprising an acid addition salt according to any embodiment of the first or second aspect of the present invention.

In preferred embodiments the dosage form comprising between 5 mg and 500 mg of 2R,6R-hydroxynorketamine or 2S,6S-hydroxynorketamine, or the equivalent thereof.

In particularly preferred embodiments the dosage is a solid oral dosage form. Preferably the solid oral dosage form is selected from a capsule and a tablet.

In embodiments of the invention the dosage form is a solid oral dosage form comprising a blend of one or more diluent. In preferred embodiments the dosage form is a tablet and the blend of one or more diluent comprises microcrystalline cellulose. In preferred embodiments the dosage form is a capsule and the capsule shell comprises a constituent selected from gelatin and hydroxypropyl methylcellulose.

DETAILED DESCRIPTION OF THE INVENTION

Figure 1A:
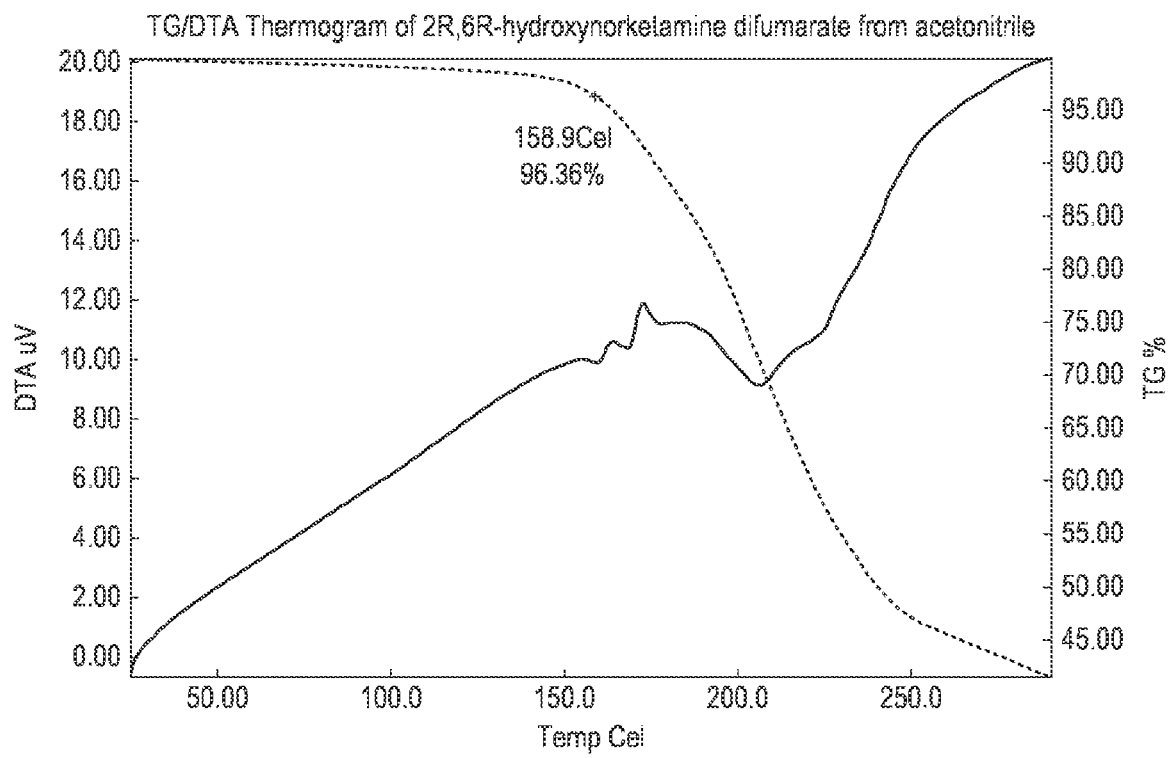
FIGS. 1A to 1F: shows TG/DTA thermogram of 2R,6R-hydroxynorketamine crystalline salt forms according to the present invention

Throughout this specification, one or more aspect of the invention may be combined with one or more features described in the specification to define distinct embodiments of the invention.

References herein to a singular of a noun encompass the plural of the noun, and vice-versa, unless the context implies otherwise.

As used herein, the term '2R,6R-hydroxynorketamine' and '2S,6S-hydroxynorketamine' refer to 2R,6R-2-(2-Chlorophenyl)-2-(amino)-6-hydroxycyclohexanone and 2S,6S-2-(2-Chlorophenyl)-2-(amino)-6-hydroxycyclohexanone respectively.

As used herein —H means a covalently bonded hydrogen.

As used herein —OH means a covalently bonded hydroxyl.

As used herein =O taken with the carbon to which it is bonded means a carbonyl group.

As used herein —COOH means a carboxylic acid group.

As used herein C=C means an olefin, in other words a carbon-carbon double bond.

As used herein the term 'chiral' means a structure which is not superimposable on its mirror image.

As used herein the term 'homochiral' means refers to a composition that comprises substantially one enantiomer of a chiral material.

An aspect of the present invention provides an acid addition salt of 2R,6R-hydroxynorketamine or 2S,6S-hydroxynorketamine obtainable by reaction with an organic acid comprising either (i) two or more carboxylic acid groups, or (ii) one or more carboxylic acid groups and an amide group.

In preferred embodiments of the first aspect, the acid addition salt of claim 1 the organic acid has Formula I or II

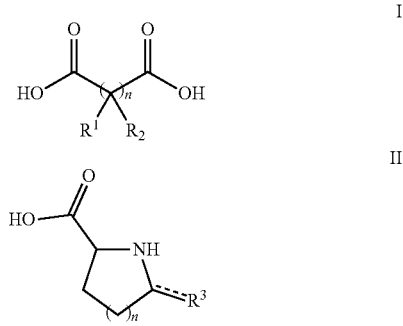

wherein n=0-3,

R$^1$ and R$^2$ are each independently selected from —H, —OH, and —COOH, and wherein when n=2 or 3, two adjacent R$^2$ groups may together represent a C=C bond, and wherein R$^3$ is —H, —OH, =O, or —COOH.

It has been discovered that 2R,6R-hydroxynorketamine and 2S,6S-hydroxynorketamine form crystalline salts readily with organic acids as described herein. Moreover, organic acids as used in the present invention may be chiral, enabling the formation of pharmaceutically acceptable salt to take part in chiral resolution of the active agent.

In embodiments of the present invention, the acid addition salt is obtainable with an organic acid having Formula III, IV or V:

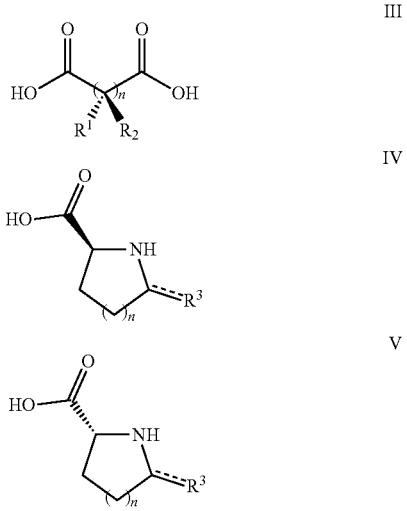

wherein n=0-3,

R$^1$ and R$^2$ are each independently selected from —H, —OH, and —COOH, wherein at least one pair of R$^1$ and R$^2$ are different, and wherein when n=2 or 3, two adjacent R$^2$ groups may together represent a C═C bond, and wherein R$^3$ is —H, —OH, ═O, or —COOH.

In embodiments of the invention the acid addition salt is obtainable with an organic acid of Formula I, wherein n=1 or 2, and wherein each R$^1$ is H, one or both R$^2$ is —OH and any remaining R$^2$ is —H.

In embodiments of the invention the acid addition salt is obtainable with an organic acid of Formula I, wherein n=2 or 3, and wherein each R$^1$ is H, two adjacent R$^2$ groups are taken together to represent a C═C bond, and any remaining R$^2$ is —H.

In embodiments of the invention the acid addition salt is obtainable with an organic acid of Formula I, wherein n=2, and wherein each R$^1$ is —H and both R$^2$ groups are taken together to represent a C═C bond.

In embodiments of the invention the acid addition salt is obtainable by reaction with an organic acid of Formula II, wherein n=1 or 2, and wherein R$^3$ is ═O.

In preferred embodiments of the first aspect of the present invention, the acid addition salt is selected from aspartic acid, citric acid, fumaric acid, glutaric acid, glutamic acid, hippuric acid, malic acid, maleic acid, mucic acid, oxalic acid, pyroglutamic acid, succinic acid, and tartaric acid.

In preferred embodiments of the first aspect of the present invention, the acid addition salt is selected from citric acid, L-tartaric acid, D-tartaric acid, L-malic acid, D-malic acid, fumaric acid, D-pyroglutamic acid, and L-pyroglutamic acid.

In preferred embodiments of the first aspect the organic acid is homochiral.

In preferred embodiments of the first aspect of the present invention, the acid addition salt is selected from 2R,6R-hydroxynorketamine L-tartrate, 2S,6S-hydroxynorketamine D-tartrate, 2R,6R-hydroxynorketamine difumarate, 2S,6S-hydroxynorketamine difumarate, 2R,6R-hydroxynorketamine D-pyroglutamate, 2S,6S-hydroxynorketamine D-pyroglutamate, 2R,6R-hydroxynorketamine L-pyroglutamate, 2S,6S-hydroxynorketamine L-pyroglutamate, 2R,6R-hydroxynorketamine L-malate, and 2S,6S-hydroxynorketamine D-malate.

In preferred embodiments of the first aspect of the present invention, the acid addition salt is in substantially crystalline form.

An aspect of the present invention provides a crystalline acid addition salt of 2R,6R-hydroxynorketamine or 2S,6S-hydroxynorketamine having an X-ray powder diffraction pattern comprising characteristic peaks expressed in degrees 2-theta at positions 19.2, 26.4 and 31.5.

In preferred embodiments of the second aspect the crystalline acid addition salt of 2R,6R-hydroxynorketamine or 2S,6S-hydroxynorketamine having an X-ray powder diffraction pattern further comprising characteristic peaks expressed in degrees 2-theta at positions 14.1, 16.9, 23.5, 24.0 and 29.9.

In preferred embodiments of the second aspect the acid addition salt is obtainable according to the first aspect of the present invention.

In embodiments the acid addition salt is selected from 2R,6R-hydroxynorketamine L-tartrate and 2S,6S-hydroxynorketamine D-tartrate and displays an X-ray powder diffraction pattern comprising characteristic peaks expressed in degrees 2-theta at positions 22.7, 25.7 and 28.7.

In embodiments the acid addition salt is selected from 2R,6R-hydroxynorketamine L-tartrate and 2S,6S-hydroxynorketamine D-tartrate and displays an X-ray powder diffraction pattern further comprising characteristic peaks expressed in degrees 2-theta at positions 6.5 and 12.8.

In embodiments the acid addition salt is selected from 2R,6R-hydroxynorketamine L-tartrate and 2S,6S-hydroxynorketamine D-tartrate and displays an X-ray powder diffraction pattern further comprising characteristic peaks expressed in degrees 2-theta at positions 10.2, 17.2, 20.3, 21.2, 21.9 and 30.5, and wherein the acid addition salt is anhydrous. In embodiments the anhydrous 2R,6R-hydroxynorketamine L-tartrate or 2S,6S-hydroxynorketamine D-tartrate has an X-ray powder diffraction pattern further comprising characteristic peaks expressed in degrees 2-theta at positions 11.4, 13.8, 16.2, 26.5, 26.7, 29.5, 31.3 and 32.6.

In embodiments the acid addition salt is selected from 2R,6R-hydroxynorketamine L-tartrate and 2S,6S-hydroxynorketamine D-tartrate and displays an X-ray powder diffraction pattern further comprising characteristic peaks expressed in degrees 2-theta at positions 8.8, 17.6, 23.7, 25.5, 25.6, 28.4 and 30.9, and wherein the acid addition salt is hydrated. In embodiments the anhydrous 2R,6R-hydroxynorketamine L-tartrate or 2S,6S-hydroxynorketamine D-tartrate has an X-ray powder diffraction pattern further comprising characteristic peaks expressed in degrees 2-theta at positions 13.7, 15.0, 18.6, 19.8, 21.4, 23.2, 29.2, 32.2 and 34.5.

In embodiments the acid addition salt is selected from anhydrous 2R,6R-hydroxynorketamine L-tartrate and anhydrous 2S,6S-hydroxynorketamine D-tartrate and displays an X-ray powder diffraction pattern comprising characteristic peaks expressed in degrees 2-theta at the following positions:

Anhydrous L-Tartrate

| Peak | Degrees 2-theta |
| --- | --- |
| 1 | 6.5 |
| 2 | 10.2 |
| 3 | 11.4 |
| 4 | 12.8 |
| 5 | 13.8 |
| 6 | 15.5 |
| 7 | 16.2 |
| 8 | 17.2 |
| 9 | 19.2 |
| 10 | 20.3 |
| 11 | 20.8 |
| 12 | 21.2 |
| 13 | 21.9 |
| 14 | 22.7 |
| 15 | 24.4 |
| 16 | 25.1 |
| 17 | 25.7 |
| 18 | 26.5 |
| 19 | 26.7 |
| 20 | 28.2 |
| 21 | 28.7 |
| 22 | 29.5 |
| 23 | 30.5 |
| 24 | 31.3 |
| 25 | 32.6 |
| 26 | 34.7 |

In embodiments the acid addition salt is selected from hydrated 2R,6R-hydroxynorketamine L-tartrate and hydrated 2S,6S-hydroxynorketamine D-tartrate and displays an X-ray powder diffraction pattern comprising characteristic peaks expressed in degrees 2-theta at the following positions:

Hydrated L-Tartrate

| Peak | Degrees 2-theta |
|---|---|
| 1 | 6.5 |
| 2 | 8.8 |
| 3 | 12.8 |
| 4 | 13.7 |
| 5 | 14.1 |
| 6 | 15.0 |
| 7 | 16.8 |
| 8 | 17.6 |
| 9 | 18.6 |
| 10 | 19.2 |
| 11 | 19.6 |
| 12 | 19.8 |
| 13 | 21.4 |
| 14 | 22.7 |
| 15 | 23.2 |
| 16 | 23.5 |
| 17 | 23.6 |
| 18 | 23.7 |
| 19 | 25.5 |
| 20 | 25.6 |
| 21 | 25.7 |
| 22 | 26.4 |
| 23 | 28.4 |
| 24 | 28.7 |
| 25 | 29.2 |
| 26 | 29.8 |
| 27 | 30.2 |
| 28 | 30.9 |
| 29 | 31.6 |
| 30 | 32.2 |
| 31 | 33.4 |
| 32 | 34.1 |
| 33 | 34.5 |

In embodiments the acid addition salt is selected from 2R,6R-hydroxynorketamine difumarate and 2S,6S-hydroxynorketamine difumarate and displays an X-ray powder diffraction pattern comprising characteristic peaks expressed in degrees 2-theta at positions 11.7, 12.4, 22.5 and 22.8.

In embodiments the acid addition salt is selected from 2R,6R-hydroxynorketamine difumarate and 2S,6S-hydroxynorketamine difumarate and displays an X-ray powder diffraction pattern further comprising characteristic peaks expressed in degrees 2-theta at positions 14.7, 16.5, 18.8, 26.8 and 29.4.

In embodiments the acid addition salt is selected from 2R,6R-hydroxynorketamine difumarate and 2S,6S-hydroxynorketamine difumarate and displays an X-ray powder diffraction pattern further comprising characteristic peaks expressed in degrees 2-theta at positions 10.2, 21.4, 23.2, 25.7, and 29.7. In embodiments the acid addition salt is selected from 2R,6R-hydroxynorketamine difumarate and 2S,6S-hydroxynorketamine difumarate and displays an X-ray powder diffraction pattern further comprising characteristic peaks expressed in degrees 2-theta at positions 18.3, 20.4, 31.0 and 33.0. In embodiments the acid addition salt is selected from 2R,6R-hydroxynorketamine difumarate and 2S,6S-hydroxynorketamine difumarate and displays an X-ray powder diffraction pattern comprising characteristic peaks expressed in degrees 2-theta at the following positions:

Difumarate

| Peak | Degrees 2-theta |
|---|---|
| 1 | 10.2 |
| 2 | 11.7 |
| 3 | 12.1 |
| 4 | 12.4 |
| 5 | 13.7 |
| 6 | 14.1 |
| 7 | 14.7 |
| 8 | 15.2 |
| 9 | 15.6 |
| 10 | 16.5 |
| 11 | 16.9 |
| 12 | 18.0 |
| 13 | 18.3 |
| 14 | 18.8 |
| 15 | 19.2 |
| 16 | 19.5 |
| 17 | 20.4 |
| 18 | 20.8 |
| 19 | 21.4 |
| 20 | 22.0 |
| 21 | 22.5 |
| 22 | 22.8 |
| 23 | 23.2 |
| 24 | 23.5 |
| 25 | 24.0 |
| 26 | 24.3 |
| 27 | 24.5 |
| 28 | 24.6 |
| 29 | 24.7 |
| 30 | 24.9 |
| 31 | 25.2 |
| 32 | 25.7 |
| 33 | 26.4 |
| 34 | 26.5 |
| 35 | 26.8 |
| 36 | 27.0 |
| 37 | 27.4 |
| 38 | 27.7 |
| 39 | 28.1 |
| 40 | 28.8 |
| 41 | 29.0 |
| 42 | 29.4 |
| 43 | 29.7 |
| 44 | 29.9 |
| 45 | 30.3 |
| 46 | 31.0 |
| 47 | 31.5 |
| 48 | 31.9 |
| 49 | 32.5 |
| 50 | 33.0 |
| 51 | 33.5 |
| 52 | 34.7 |

In embodiments the acid addition salt is selected from 2R,6R-hydroxynorketamine L-malate and 2S,6S-hydroxynorketamine D-malate and displays an X-ray powder diffraction pattern comprising a characteristic peak expressed in degrees 2-theta at position 23.1.

In embodiments the acid addition salt is selected from 2R,6R-hydroxynorketamine L-pyroglutamate and 2S,6S-hydroxynorketamine D-pyroglutamate and displays an X-ray powder diffraction pattern comprising characteristic peaks expressed in degrees 2-theta at the following positions:

L-Pyroglutamate

| Peak | Degrees 2-theta |
|---|---|
| 1 | 9.0 |
| 2 | 12.0 |
| 3 | 12.8 |
| 4 | 13.6 |
| 5 | 13.8 |
| 6 | 14.1 |
| 7 | 14.3 |
| 8 | 15.2 |
| 9 | 16.6 |
| 10 | 17.6 |
| 11 | 17.8 |
| 12 | 18.1 |
| 13 | 19.9 |
| 14 | 20.3 |
| 15 | 20.8 |
| 16 | 21.0 |
| 17 | 21.4 |
| 18 | 21.8 |
| 19 | 22.4 |
| 20 | 22.7 |
| 21 | 23.1 |
| 22 | 23.8 |
| 23 | 24.6 |
| 24 | 25.0 |
| 25 | 25.3 |
| 26 | 25.5 |
| 27 | 25.7 |
| 28 | 26.2 |
| 29 | 26.5 |
| 30 | 27.3 |
| 31 | 27.8 |
| 32 | 28.2 |
| 33 | 28.5 |
| 34 | 28.7 |
| 35 | 28.9 |
| 36 | 29.3 |
| 37 | 30.1 |
| 38 | 30.6 |
| 39 | 31.1 |
| 40 | 31.5 |
| 41 | 32.3 |
| 42 | 32.7 |
| 43 | 33.1 |
| 44 | 33.3 |
| 45 | 33.7 |
| 46 | 33.9 |
| 47 | 34.1 |
| 48 | 34.6 |

In preferred embodiments the acid addition salt is obtained by precipitation or crystallisation from an organic solvent selected from acetonitrile, isopropyl acetate, t-butyl methyl ether, ethyl acetate, and diisopropyl ether. A further aspect of the present invention provides a dosage form comprising an acid addition salt according to any embodiment of the first or second aspect of the present invention.

As used herein, the term 'solid oral dosage form' is defined as a solid pharmaceutical formulation which can be swallowed whole, chewed and swallowed, or dissolved, dispersed or absorbed via the oral cavity. Solid oral dosage forms include tablets, pills, capsules, caplets, orodispersible tablets, powders, granules and gums. Solid oral dosage forms are not taken to include liquid or aerosol formulations, powders for inhalation, or powders for injection.

Solid oral dosage forms according to the present invention may be prepared by mixing the principle active agent(s) with a pharmaceutical carrier, e.g. corn starch, lactose, sucrose, sorbitol, talc, stearic acid, magnesium stearate, or dicalcium phosphate, and other pharmaceutical diluents, e.g. water, to form a solid preformulation composition containing a homogenous mixture of the active agent(s). When referring to these preformulation compositions as homogenous, it is meant that the active agent is dispersed evenly throughout the composition so that the composition may be readily subdivided into equally effective dosage forms such as tablets, pills and capsules. The solid preformulation composition is then subdivided into unit dosage forms of the type described above.

In preferred embodiments of the present invention, the solid oral dosage form is provided in a unit dose containing between 5 mg and 500 mg of the acid addition salt of 2R,6R-hydroxynorketamine or 2S,6S-hydroxynorketamine as defined herein.

Quantities of weight provided herein refer to the free-form equivalent of a compound of the present invention. For example a unit dose of 500 mg 2R,6R-hydroxynorketamine hydrochloride, contains the mass equivalent of 500 mg freebase 2R,6R-hydroxynorketamine, and has an actual mass of 576 mg.

In preferred embodiments the dosage form comprising between 5 mg and 500 mg of 2R,6R-hydroxynorketamine or 2S,6S-hydroxynorketamine, or the equivalent thereof.

In particularly preferred embodiments the dosage is a solid oral dosage form. Preferably the solid oral dosage form is selected from a capsule and a tablet.

In embodiments of the invention the dosage form is a solid oral dosage form comprising a blend of one or more diluent. In preferred embodiments the dosage form is a tablet and the blend of one or more diluent comprises microcrystalline cellulose. In preferred embodiments the dosage form is a capsule and the capsule shell comprises a constituent selected from gelatin and hydroxypropyl methylcellulose.

Synthetic Schemes

Definitions Used in Synthetic Schemes:

As used herein 'mCPBA' refers to meta-chloroperoxybenzoic acid.

As used herein 'syn' refers to the configuration of compounds of Formula I having substituents on the same face of the cyclohexanone ring resulting from addition of the alpha-hydroxyl onto the same face as the amine group. Thus the absolute stereochemistry of compounds of Formula VI is R,R or S,S.

As used herein 'enol' refers to a chemical moiety having an alkene with a hydroxyl group attached to one end of the alkene double bond. 'Enolate' refers to an enol with the hydroxyl proton removed.

As used herein 'dihydroxylating agent' refers to one or more chemical substances that is capable of adding two hydroxyl groups across the double bond of an enol or enolate.

As used herein the term 'alpha-hydroxylating agent' refers to one or more chemical substances that is capable of adding a hydroxyl group to an aliphatic carbon next to a carbonyl group.

As used herein the term 'nitrogen protecting group' refers to a moiety which can be reversibly added to the nitrogen atom of an amine group to achieve chemical selectivity in one or more subsequent reaction.

As used herein the term 'alkyl' means a hydrocarbon moiety having the general formula $C_nH_{2n+1}$. The term encompasses methyl (also referred to as Me), ethyl (Et), isopropyl (iPr, $^i$Pr, or i-Pr), tert-butyl (tBu, $^t$Bu, or t-Bu).

As used herein the term 'silyl' means a hydrosilicon moiety having the general formula $Si_nH_{2n+1}$. The term encompasses trimethylsilyl (TMS) and triethylsilyl (TES).

As used herein the term 'Boc' means tert-butoxycarbonyl.

As used herein the term 'MoOPH' refers to oxodiperoxymolybdenum(pyridine)-(hexamethylphosphoric triamide).

As used herein the term '$OsO_4$' means osmium tetroxide and its chemical equivalents.

As used herein the term '$RuO_4$' means ruthenium tetroxide and its chemical equivalents.

As used herein the term '$I_2$' refers to elemental iodine.

As used herein the term 'oxone' refers to potassium peroxymonosulfate, also known as MPS.

As used herein the term 'NaOCl' refers to sodium hypochlorite, also known as bleach.

As used herein the term 'oxaziridine' refers to a compound which features a three-membered heterocycle containing oxygen, nitrogen, and carbon.

As used herein the term 'AD-mix alpha' refers to a reagent system used in Sharpless asymmetric dihydroxylation consisting of hydroquinine 1,4-phthalazinediyl diether (0.16 mole %), potassium carbonate (49.88 mole %) potassium ferricyanide (49.88 mole %) potassium osmate dihydrate (0.07 mole %).

As used herein the term 'AD-mix beta' refers to a reagent system used in Sharpless asymmetric dihydroxylation consisting of hydroquinidine 1,4-phthalazinediyl diether (0.16 mole %), potassium carbonate (49.88 mole %) potassium ferricyanide (49.88 mole %) potassium osmate dihydrate (0.07 mole %).

Scheme 1 describes a general synthesis applicable to manufacturing 6-hydroxynorketamine and analogues thereof. Analogous acid addition salts to the salts of the present invention may be made by reacting a compound of Formula VI with an organic acid selected from the organic acids of Formula I, II, III, IV or V:

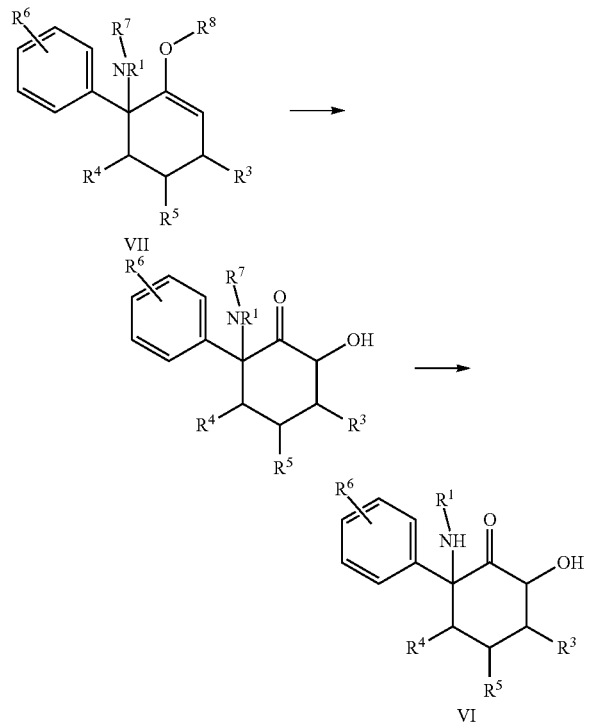

Scheme 1 wherein $R^1$ is H or $C_1$-$C_4$ alkyl; $R^3$ is H or $C_1$-$C_4$ alkyl; $R^4$ is H or $C_1$-$C_4$ alkyl; $R^5$ is H or $C_1$-$C_4$ alkyl; and $R^6$ represents 0, 1, 2, 3, 4 or 5 haloatoms each independently selected from F, Cl, Br, I, and wherein the —OH and the —$NHR^1$ are syn to one another; wherein the method comprises the step of reacting an enolate or an enol ether of Formula II wherein $R^1$, $R^3$, $R^4$, $R^5$, and $R^6$ are as in the compound of Formula I, with a dihydroxylating agent or an alpha-hydroxylating agent, wherein $R^7$ is H or a nitrogen protecting group; and $R^8$ is selected from trialkylsilyl, $C_1$-$C_4$ alkyl, —(CO)($C_1$-$C_4$ alkyl), or wherein $R^8$ represents a cationic counterion to enolate, and wherein when $R^7$ is a nitrogen protecting group, the method further comprises the step of removing $R^7$.

In a preferred embodiments of Scheme 1, the alpha-hydroxylating agent does not comprise mCPBA.

In preferred embodiments of the Scheme 1 $R^1$ is H or Me. In preferred embodiments $R^3$ is H or Me. In preferred embodiments $R^4$ is H or Me. In preferred embodiments $R^3$ and $R^4$ are both Me. In preferred embodiments $R^5$ is selected from H, Me, i-Pr or t-Bu. In preferred embodiments either $R^5$ is i-Pr or t-Bu or one or both of $R^3$ and $R^4$ are Me.

In preferred embodiments $R^6$ represents one haloatom selected from F, Cl, Br, and I, which is ortho to the C—C bond linking the aryl group to the cyclohexanone. In preferred embodiments $R^6$ represents two haloatoms selected from F, Cl, Br, and I, preferably one or both of which are ortho to the C—C bond linking the aryl group to the cyclohexanone. In preferred embodiments $R^6$ represents one or two haloatoms which are ortho to the C—C bond linking the aryl group to the cyclohexanone. In preferred embodiments $R^6$ represents one haloatom selected from F, Cl, Br, and I. In preferred embodiments $R^6$ represents two separate haloatoms independently selected from F, Cl, Br, and I, preferably one or both of which are ortho to the C—C bond linking the aryl group to the cyclohexanone. In preferred embodiments $R^6$ represents three separate haloatoms independently selected from F, Cl, Br, and I, preferably one or more of which are ortho to the C—C bond linking the aryl group to the cyclohexanone. In preferred embodiments $R^6$ represents three separate haloatoms independently selected from F, Cl, Br, and I, wherein two haloatoms are ortho and one is para to the C—C bond linking the aryl group to the cyclohexanone. In preferred embodiments $R^6$ represents the same haloatom selected from F, Cl, Br, and I. In preferred embodiments $R^6$ represents Cl. In preferred embodiments $R^6$ represents one Cl. In preferred embodiments $R^6$ represents two separate Cl, preferably one or more of which are ortho to the C—C bond linking the aryl group to the cyclohexanone. In preferred embodiments $R^6$ represents three separate Cl, preferably one or more of which are ortho to the C—C bond linking the aryl group to the cyclohexanone. In preferred embodiments at least one haloatom represented by $R^6$ is Cl. In preferred embodiments, all haloatoms represented by $R^6$ are Cl.

In preferred analogues of the present invention, the acid addition salt is obtainable by reaction of a compound of Formula I selected from Compounds 1-36 and an organic acid selected from Formulae I, II, III, IV and V. Preferably the acid addition salt of Compounds 1-36 is the L-pyroglutamate or the D-pyroglutamate.

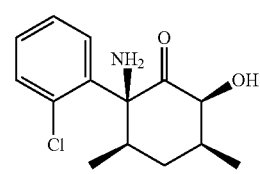

1

-continued
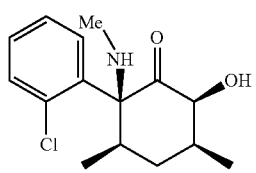
2
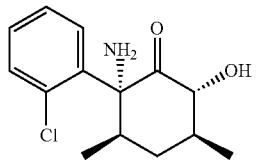
3
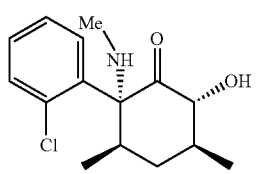
4
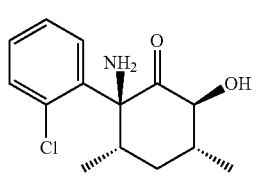
5
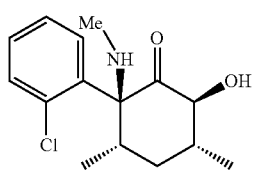
6
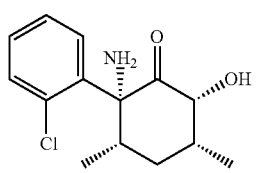
7
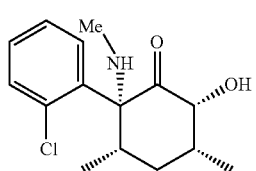
8
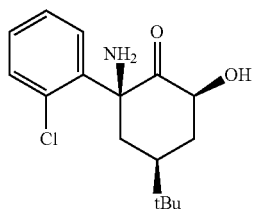
9
-continued
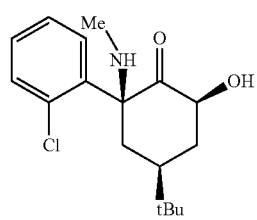
10
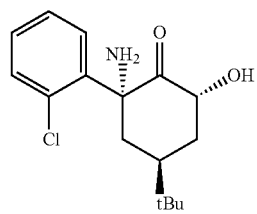
11
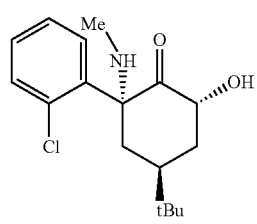
12
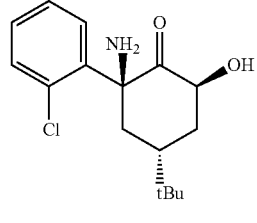
13
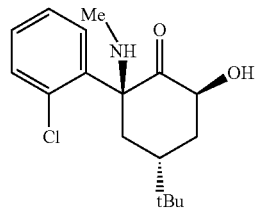
14
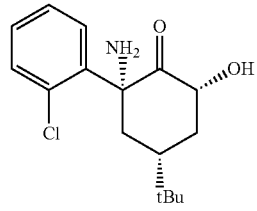
15
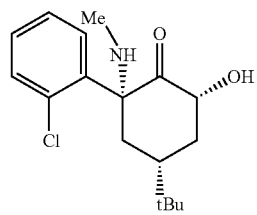
16

17
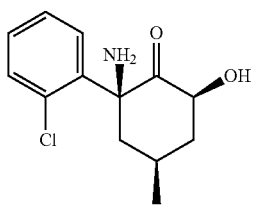
18
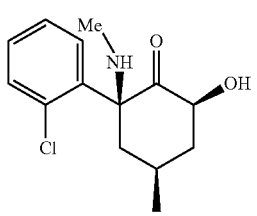
19
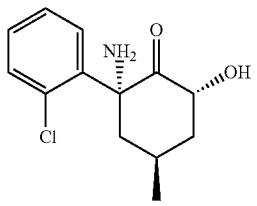
20
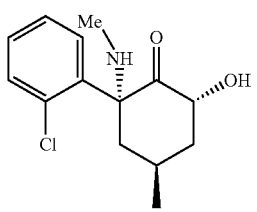
21
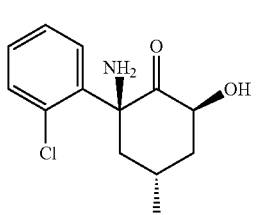
22
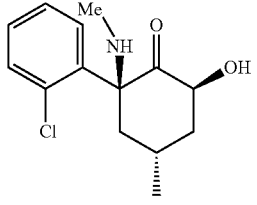
23
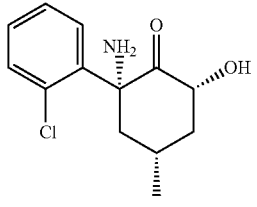
24
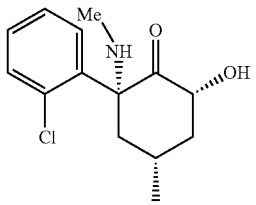
25
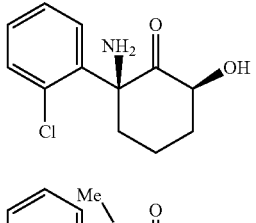
26
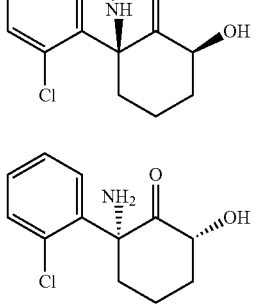
27
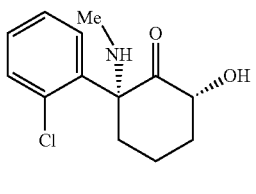
28
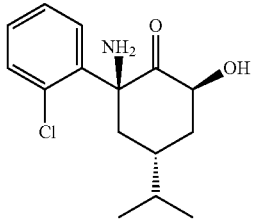
29
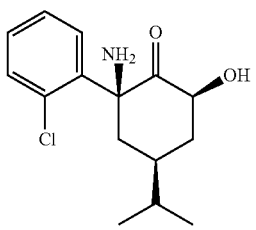
30
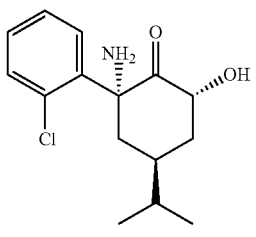
31

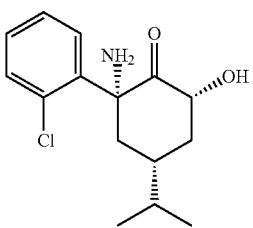

32

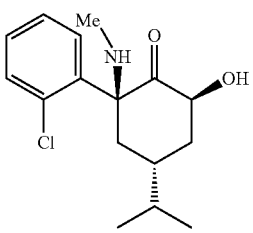

33

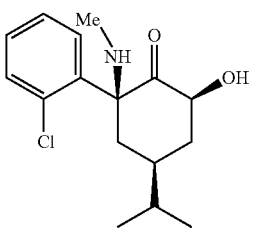

34

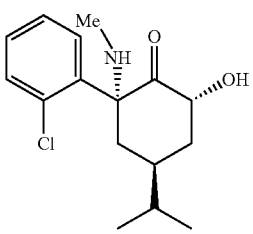

35

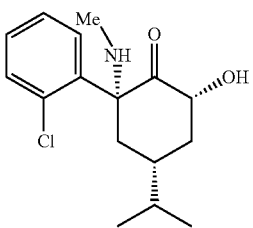

36

In preferred embodiments of Scheme 1, R⁷ is a nitrogen protecting group. In preferred embodiments of the synthetic scheme, R⁷ is Boc.

In preferred embodiments of the synthetic scheme R⁸ is a silyl enol ether, preferably selected from TMS and TES.

In preferred embodiments of the synthetic scheme the dihydroxylating agent comprises an oxidising agent selected from MoOPH, $OsO_4$, $RuO_4$, and $I_2$.

In preferred embodiments of the synthetic scheme the alpha-hydroxylating agent comprises an oxidising agent selected from oxone, NaOCl, oxaziridine, lead (IV) acetate, and hypoflorous acid in acetonitrile.

In preferred embodiments of Scheme 1 the dihydroxylating agent comprises AD-mix alpha. In preferred aspects of the first aspect of the present invention the dihydroxylating agent comprises AD-mix beta.

In preferred embodiments of Scheme 1 the alpha-hydroxylating agent comprises an N-sulfonyloxaziridine.

In preferred embodiments of Scheme 1 the dihydroxylating agent comprises $OsO_4$, potassium ferricyanide and a chiral auxiliary selected from a dihydroquinidine and a dihydroquinine.

In a particularly preferred embodiment of Scheme 1 the compound of Formula I is 2R,6R-hydroxynorketamine, the compound of Formula II is Compound 37; and the dihydroxylating agent comprises $OsO_4$, postassium ferricyanide and a chiral auxiliary selected from a dihydroquinidine and a dihydroquinine.

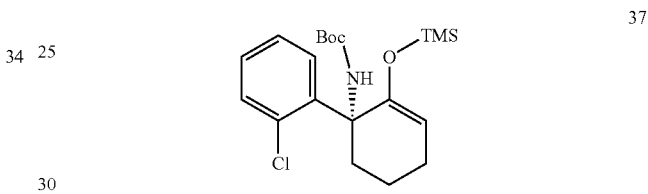

37

It has been found that Scheme 1 is effective in preparing a compound of Formula I in high yield wherein the —OH and the —NHR¹ are syn to one another irrespective of which chiral auxiliary of dihydroquinidine and dihydroquinine is present in the reaction.

In preferred embodiments the Boc protecting group is removed by treating with HCl in cyclopentyl methyl ether (CPME).

In a preferred embodiment of Scheme 1, the compound of Formula I is 2R,6R-hydroxynorketamine, wherein the compound of Formula II is Compound 38; and wherein the alpha-hydroxylating agent comprises the Davis's oxaziridine of Compound 39

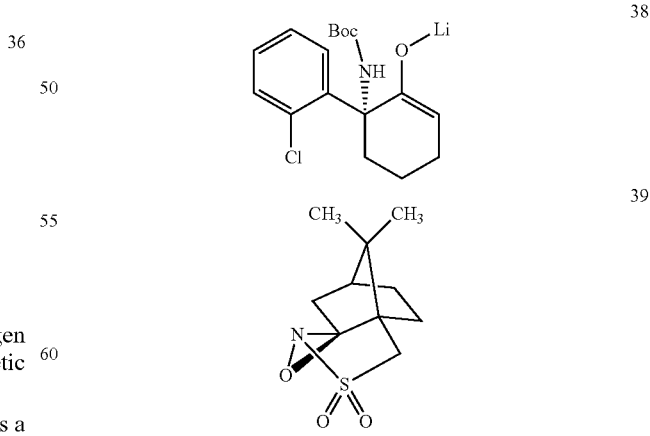

38

39

Scheme 2 describes a method of synthesising a compound of Formula VIII suitable for synthesizing the enolate or enol ether of Formula VII, Scheme 2

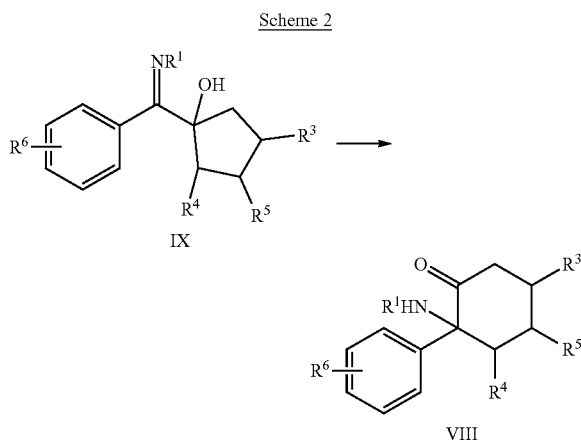

wherein $R^1$ is H or $C_1$-$C_4$ alkyl; $R^3$ is H or $C_1$-$C_4$ alkyl; $R^4$ is H or $C_1$-$C_4$ alkyl; $R^5$ is H or $C_1$-$C_4$ alkyl; and $R^6$ represents 0, 1, 2, 3, 4 or 5 haloatoms each independently selected from F, Cl, Br, I; wherein said method comprises the step of refluxing a compound of Formula IV in a solvent comprising a $C_1$-$C_6$ alcohol, wherein $R^1$, $R^3$, $R^4$, $R^5$, and $R^6$ are as in the compound of Formula VIII.

In preferred embodiments of Scheme 2 the $C_1$-$C_6$ alcohol is isobutanol.

In preferred embodiments of Scheme 2 the step of refluxing a compound of Formula IX in a solvent comprising a $C_1$-$C_6$ alcohol is carried out in the presence of a Lewis acid. Preferably the Lewis acid is an azaphilic Lewis acid.

In preferred embodiments of Scheme 2 the step of refluxing a compound of Formula IX in a solvent comprising a $C_1$-$C_6$ alcohol is carried out in the presence of a chiral Lewis acid.

Scheme 3 provides a method of synthesising a compound of Formula VIII suitable for synthesizing the enolate or enol ether of Formula VII, Scheme 3

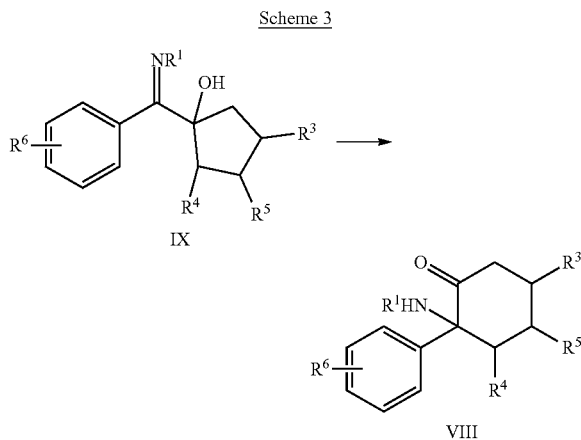

wherein $R^1$ is H or $C_1$-$C_4$ alkyl; $R^3$ is H or $C_1$-$C_4$ alkyl; $R^4$ is H or $C_1$-$C_4$ alkyl; $R^5$ is H or $C_1$-$C_4$ alkyl; and $R^6$ represents 0, 1, 2, 3, 4 or 5 haloatoms each independently selected from F, Cl, Br, I; wherein said method comprises the step of heating a compound of Formula IX in the presence of a Lewis acid, wherein $R^1$, $R^3$, $R^4$, $R^5$, and $R^6$ are as in the compound of Formula VIII. Preferably the Lewis acid is an azaphilic Lewis acid. In preferred embodiments of the fourth aspect the Lewis acid is a chiral Lewis acid.

In preferred embodiments of Schemes 2 or 3, the compound of Formula IX and the Lewis acid are dissolved in an aprotic solvent. Suitable aprotic solvents include diethyl ether, THF, DMF and DMSO.

In preferred embodiments of Schemes 2 or 3, the Lewis acid comprises boron or a metal atom selected from copper, aluminium, zinc, scandium, indium, and titanium. Preferably the Lewis acid comprises boron, copper or zinc, for example Cu(OTf)$_2$ or Zn(OTf)$_2$.

In preferred embodiments of Schemes 2 or 3, the Lewis acid comprises one or more chiral ligand. Preferred chiral ligands include bis(oxazoline) ligands (eg. BOX and PyBOX), 1,1'-Bi-2-naphthol ligands, 2,2'-bis(diphenylphosphino)-1,1'-binaphthyl ligands, α,α,α',α'-tetraaryl-2,2-disubstituted 1,3-dioxolane-4,5-dimethanol ligands, phospholane ligands, and salen ligands. Examples of chiral Lewis acid catalysts for use in the third or fourth aspect of the present invention include copper (II) (−)2,2'-isopropylidenebis[(4S)-4-tert-butyl-2-oxazoline] di(triflouromethanesulfonate), copper (II) (+)2,2'-Isopropylidenebis[(4R)-4-tert-butyl-2-oxazoline] di(triflouromethanesulfonate), copper (I) (−)-2,2'-isopropylidenebis[(4S)-4-phenyl-2-oxazoline] trifluoromethanesulfonate, copper (I) (+)-2,2'-isopropylidenebis[(4S)-4-phenyl-2-oxazoline] trifluoromethanesulfonate, (R)-(+)-2-Methyl-CBS-oxazaborolidine, and (S)-(−)-2-Methyl-CBS-oxazaborolidine.

In preferred embodiments of Schemes 2 or 3, $R^1$ is H or Me. In preferred embodiments $R^3$ is H or Me. In preferred embodiments $R^4$ is H or Me. In preferred embodiments $R^3$ and $R^4$ are both Me. In preferred embodiments $R^5$ is selected from H, Me, i-Pr or t-Bu. In preferred embodiments either $R^5$ is i-Pr or t-Bu or one or both of $R^3$ and $R^4$ are Me.

In preferred embodiments $R^6$ represents one haloatom selected from F, Cl, Br, and I, which is ortho to the C—C bond linking the aryl group to the cyclohexanone. In preferred embodiments $R^6$ represents two haloatoms selected from F, Cl, Br, and I, preferably one or both of which are ortho to the C—C bond linking the aryl group to the cyclohexanone. In preferred embodiments $R^6$ represents one or two haloatoms which are ortho to the C—C bond linking the aryl group to the cyclohexanone. In preferred embodiments $R^6$ represents one haloatom selected from F, Cl, Br, and I. In preferred embodiments $R^6$ represents two separate haloatoms independently selected from F, Cl, Br, and I, preferably one or both of which are ortho to the C—C bond linking the aryl group to the cyclohexanone. In preferred embodiments $R^6$ represents three separate haloatoms independently selected from F, Cl, Br, and I, preferably one or more of which are ortho to the C—C bond linking the aryl group to the cyclohexanone. In preferred embodiments $R^6$ represents three separate haloatoms independently selected from F, Cl, Br, and I, wherein two haloatoms are ortho and one is para to the C—C bond linking the aryl group to the cyclohexanone. In preferred embodiments $R^6$ represents the same haloatom selected from F, Cl, Br, and I. In preferred embodiments $R^6$ represents Cl. In preferred embodiments $R^6$ represents one Cl. In preferred embodiments $R^6$ represents two separate Cl, preferably one or more of which are ortho to the C—C bond linking the aryl group to the cyclohexanone. In preferred embodiments $R^6$ represents three separate Cl, preferably one or more of which are ortho to the C—C bond linking the aryl group to the cyclohexanone. In preferred embodiments at least one haloatom represented by $R^6$ is Cl. In preferred embodiments, all haloatoms represented by $R^6$ are Cl.

In an aspect of Schemes 2 or 3, the compound of Formula IX is synthesised by treating a compound of Formula X with NHR¹

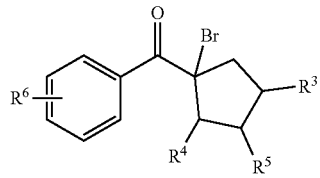

X wherein $R^3$, $R^4$, $R^5$, and $R^6$ are as in Formula IX.

In a preferred embodiment, Compound 40 is synthesised by treating Compound 41 with an excess of liquid ammonia and allowing residual ammonia to evaporate at ambient temperature and pressure. This method provides for efficient, synthesis of 40 in near quantitative yield, which can be for use in synthesis of norketamine, 2R,6R-hydroxynorketamine, or 2S,6S-hydroxynorketamine.

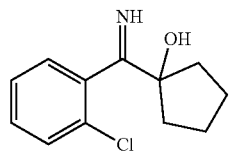

40

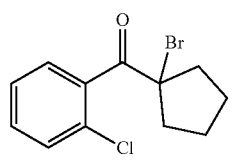

41

The general synthesis of compounds of Formula VI from readily available starting materials is provided in Scheme 4 below:

Scheme 4

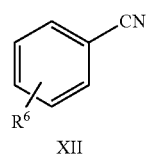

XII

1) 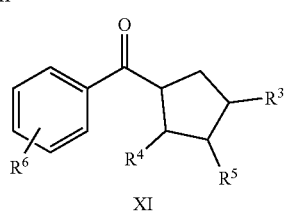
$R^3$, CuBr, THF
2) 15% $H_2SO_4$

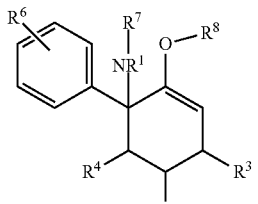

XI

CuBr₂, EtOAc
Reflux

-continued

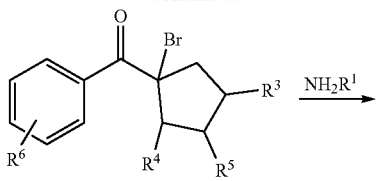

X

NH₂R¹ →

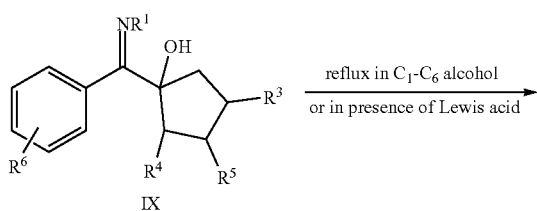

IX reflux in $C_1$-$C_6$ alcohol
or in presence of Lewis acid →

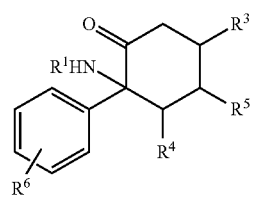

VIII

Boc₂O
NEt₃
THF
70° C.
18 h

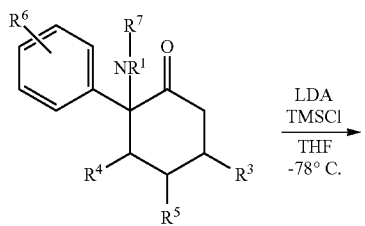

LDA
TMSCl
THF
-78° C.

AD-mix (α or β)
ᵗBuOH/H₂O
0° C. - r.t.
48 h

VII

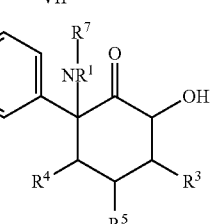

HCl
CPME

Hydroxylation syn to amine

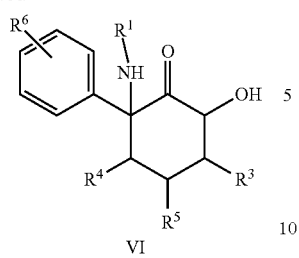
A scalable, efficient and high yielding synthesis which applies to the manufacture of 2R,6R-hydroxynorketamine or 2S,6S-hydroxynorketamine is provided in Scheme 5.
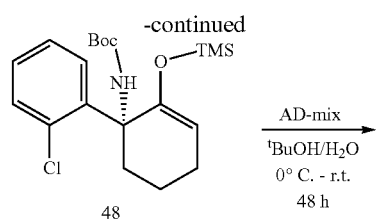
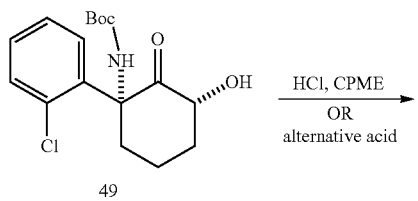
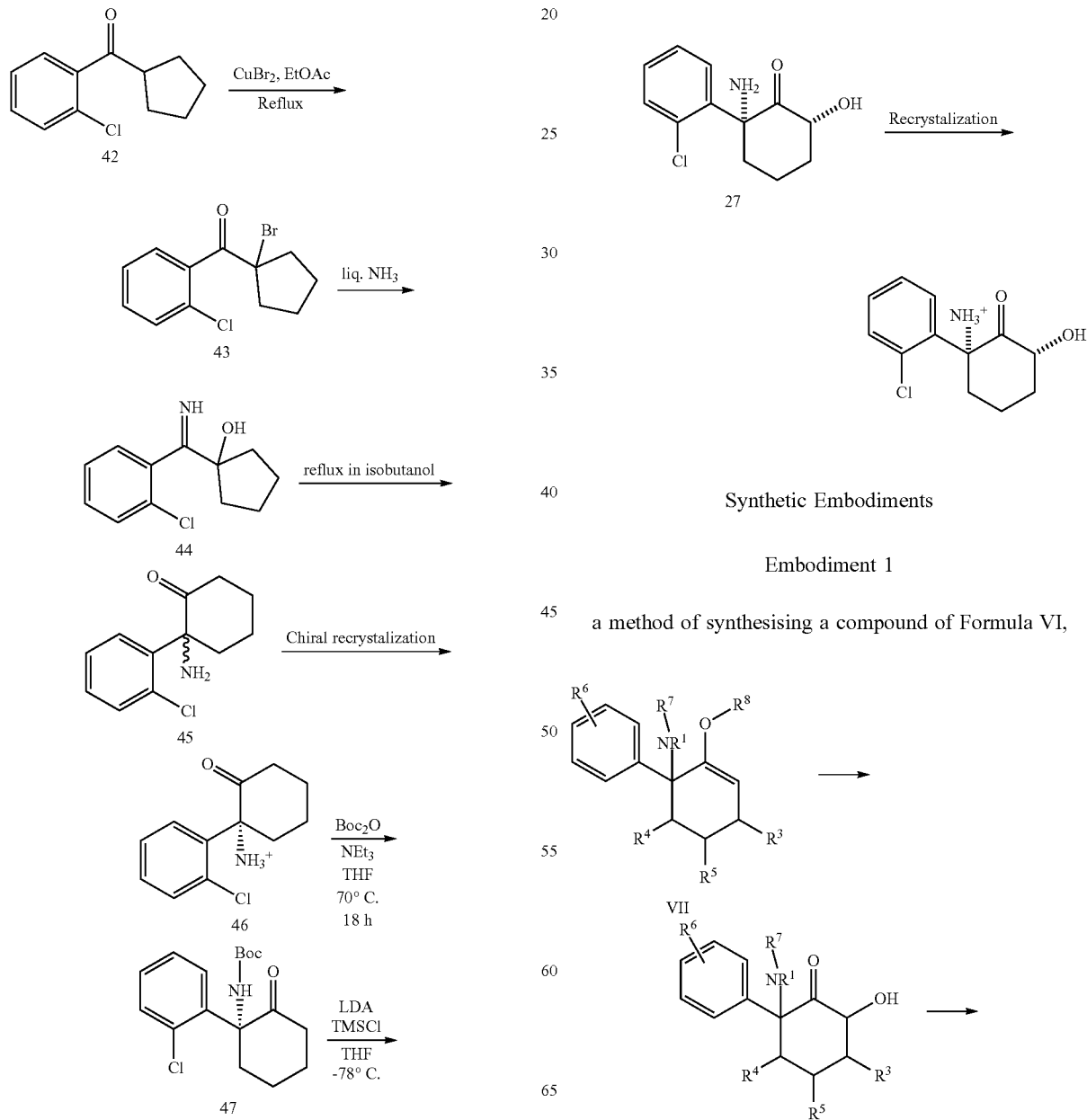
Synthetic Embodiments
Embodiment 1
a method of synthesising a compound of Formula VI, -continued

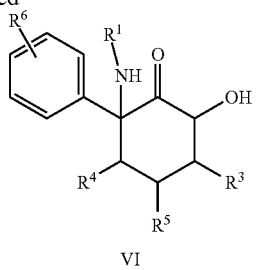

VI wherein $R^1$ is H or $C_1$-$C_4$ alkyl; $R^3$ is H or $C_1$-$C_4$ alkyl; $R^4$ is H or $C_1$-$C_4$ alkyl; $R^5$ is H or $C_1$-$C_4$ alkyl; and $R^6$ represents 0, 1, 2, 3, 4 or 5 haloatoms each independently selected from F, Cl, Br, I, and wherein the —OH and the —$NHR^1$ are syn to one another;
comprising the step of reacting an enolate or an enol ether of Formula VII wherein $R^1$, $R^3$, $R^4$, $R^5$, and $R^6$ are as in the compound of Formula VI, with a dihydroxylating agent or an alpha-hydroxylating agent, wherein $R^7$ is H or a nitrogen protecting group; and $R^8$ is selected from trialkylsilyl, $C_1$-$C_4$ alkyl, —(CO)($C_1$-$C_4$ alkyl), or wherein $R^8$ represents a cationic counterion to enolate;
wherein when $R^7$ is a nitrogen protecting group, the method further comprises the step of removing $R^7$;
with the proviso that the alpha-hydroxylating agent is not mCPBA.

Embodiment 2

The method of embodiment 1 wherein $R^1$ is H, $R^3$ is H, $R^4$ is H, $R^5$ is H, and $R^6$ is ortho-Cl.

Embodiment 3

The method of embodiment 1 or 2 wherein $R^7$ is Boc.

Embodiment 4

The method of embodiments 1-3 wherein $R^8$ is selected from TMS and TES.

Embodiment 5

The method of embodiments 1-4 wherein the dihydroxylating agent comprises an oxidising agent selected from MoOPH, $OsO_4$, $RuO_4$, and $I_2$.

Embodiment 6

The method of embodiments 1-4 wherein the alpha-hydroxylating agent comprises an oxidising agent selected from oxone, NaOCl, oxaziridine, lead (IV) acetate, and hypoflorous acid-acetonitrile.

Embodiment 7

The method of embodiment 5 wherein the dihydroxylating agent comprises AD-mix alpha.

Embodiment 8

The method of embodiment 5 wherein the dihydroxylating agent comprises AD-mix beta.

Embodiment 9

The method of embodiment 6 wherein the alpha-hydroxylating agent comprises an N-sulfonyloxaziridine.

Embodiment 10

The method of embodiment 1 wherein the compound of Formula VI is 2R,6R-hydroxynorketamine,
wherein the compound of Formula II is Compound 37; and
wherein the dihydroxylating agent comprises $OsO_4$, $K_3[Fe(CN)_6]$, and a chiral auxiliary selected from dihydroquinidine and dihydroquinine

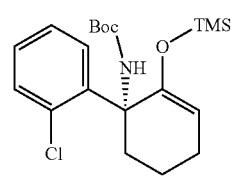

37

Embodiment 11

The method of embodiment 10 wherein the Boc protecting group is removed by treating with HCl in cyclopentyl methyl ether.

Embodiment 12

The method of embodiment 1 wherein the compound of Formula I is 2R,6R-hydroxynorketamine,
wherein the compound of Formula II is Compound 38; and
wherein the alpha-hydroxylating agent comprises the Davis's oxaziridine of Compound 39

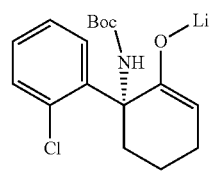

38

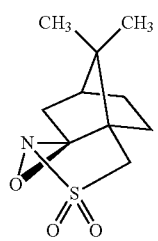

39

Embodiment 13

A method of synthesising a compound of Formula VIII suitable for synthesizing the enolate or enol ether of Formula VII,

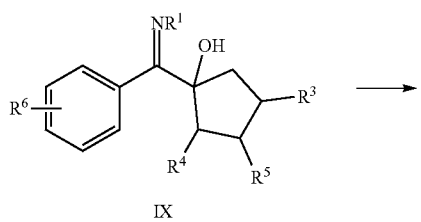

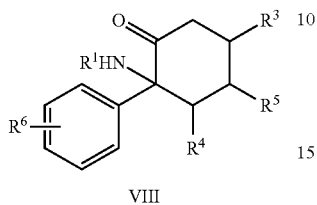

wherein R¹ is H or $C_1$-$C_4$ alkyl; R³ is H or $C_1$-$C_4$ alkyl; R⁴ is H or $C_1$-$C_4$ alkyl; R⁵ is H or $C_1$-$C_4$ alkyl; and R⁶ represents 0, 1, 2, 3, 4 or 5 haloatoms each independently selected from F, Cl, Br, I;
wherein said method comprises the step of refluxing a compound of Formula IX in a solvent comprising a $C_1$-$C_6$ alcohol, wherein R¹, R³, R⁴, R⁵, and R⁶ are as in the compound of Formula VIII.

Embodiment 14

The method of embodiment 13 wherein the $C_1$-$C_6$ alcohol is isobutanol.

Embodiment 15

The method of embodiment 13 or 14 wherein the step of refluxing a compound of Formula IV in a solvent comprising a $C_1$-$C_6$ alcohol is carried out in the presence of a Lewis acid.

Embodiment 16

A method of synthesising a compound of Formula VIII suitable for synthesizing the enolate or enol ether of Formula VII,

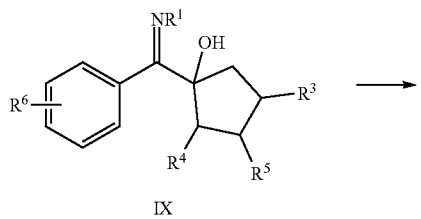

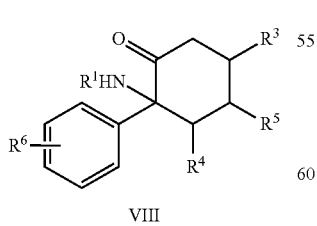

wherein R¹ is H or $C_1$-$C_4$ alkyl; R³ is H or $C_1$-$C_4$ alkyl; R⁴ is H or $C_1$-$C_4$ alkyl; R⁵ is H or $C_1$-$C_4$ alkyl; and R⁶ represents 0, 1, 2, 3, 4 or 5 haloatoms each independently selected from F, Cl, Br, I;

wherein said method comprises the step of heating a compound of Formula IX in the presence of a Lewis acid, wherein R¹, R³, R⁴, R⁵, and R⁶ are as in the compound of Formula VIII.

Embodiment 17

The method of embodiment 13-16 wherein the Lewis acid is an azaphilic Lewis acid.

Embodiment 18

The method of embodiment 13-17 wherein the Lewis acid is a chiral Lewis acid.

Embodiment 19

The method of embodiment 18 wherein the Lewis acid is selected from copper (II) (−)2,2'-isopropylidenebis[(4S)-4-tert-butyl-2-oxazoline]di(trifluoromethanesulfonate), copper (II) (+)2,2'-Isopropylidenebis[(4R)-4-tert-butyl-2-oxazoline] di(trifluoromethanesulfonate), copper (I) (−)-2,2'-isopropylidenebis[(4S)-4-phenyl-2-oxazoline] trifluoromethanesulfonate, copper (I) (+)-2,2'-isopropylidenebis[(4S)-4-phenyl-2-oxazoline] trifluoromethanesulfonate, (R)-(+)-2-Methyl-CBS-oxazaborolidine, and (S)-(−)-2-Methyl-CBS-oxazaborolidine.

Embodiment 20

The method of embodiment 13-19 wherein R¹ is H, R³ is H, R⁴ is H, R⁵ is H, and R⁶ is ortho-Cl.

Embodiment 21

The method of embodiment 13-20 wherein the compound of Formula IV is synthesised by treating a compound of Formula X with NHR¹, wherein R³, R⁴, R⁵, and R⁶ are as in Formula IX

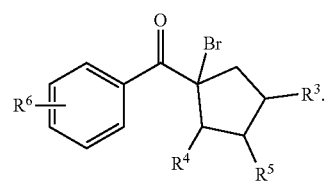

Embodiment 22

The method of embodiment 21 wherein Compound 43 is synthesised by treating Compound 44 with liquid ammonia and allowing residual ammonia to evaporate at ambient temperature and pressure.

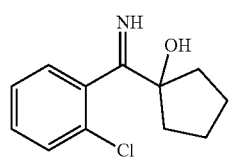

-continued

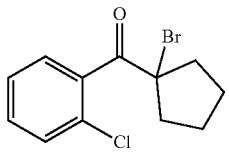

44

Embodiment 23

A method of synthesizing a compound of Formula I, wherein:
$R^1$ is H or $C_1$-$C_4$ alkyl; $R^3$ is H or $C_1$-$C_4$ alkyl; $R^4$ is H or $C_1$-$C_4$ alkyl; $R^5$ is H or $C_1$-$C_4$ alkyl; and $R^6$ represents 0, 1, 2, 3, 4 or 5 haloatoms each independently selected from F, Cl, Br, I, and wherein the —OH and the —$NHR^1$ are syn to one another, comprising the method of any of embodiments 13-22 and further comprising the method of any one of embodiments 1-12.

Embodiment 24

The intermediate of Formula XIII

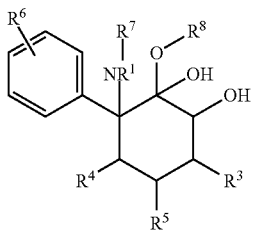

VIII wherein $R^1$ is H or $C_1$-$C_4$ alkyl; $R^3$ is H or $C_1$-$C_4$ alkyl; $R^4$ is H or $C_1$-$C_4$ alkyl; $R^5$ is H or $C_1$-$C_4$ alkyl; and $R^6$ represents 0, 1, 2, 3, 4 or 5 haloatoms each independently selected from F, Cl, Br, I; $R^7$ is H or a nitrogen protecting group; and $R^8$ is selected from trialkylsilyl, $C_1$-$C_4$ alkyl, —(CO)($C_1$-$C_4$ alkyl).

Embodiment 25

The intermediate of embodiment 24 wherein $R^1$ is H, $R^3$ is H, $R^4$ is H, $R^5$ is H, $R^6$ is ortho-Cl.

Embodiment 26

The intermediate of embodiment 24 or 25 wherein $R^7$ is Boc.

Embodiment 27

The intermediate of embodiment 24-26 wherein $R^8$ is trimethylsilyl.

Embodiment 28

The intermediate of embodiment 24-27 wherein the stereochemical configuration at the 2 and 6 position are both R.

EXAMPLES

Example 1: Synthesis of 2R,6R-hydroxynorketamine Hydrochloride (R)—N-Boc-norketamine (47)

Boc protection of norketamine was achieved with 95% yield by treating with $Boc_2O$ and triethylamine in THF at 70° C. for 16-18 hours.

1H-NMR (301 MHz, CHLOROFORM-D) δ 7.81 (d, J=6.9 Hz, 1H), 7.26 (d, J=48.2 Hz, 3H), 6.57 (s, 1H), 3.78-3.83 (m, 1H), 2.22-2.41 (m, 2H), 2.02-2.05 (m, 1H), 1.58-1.81 (m, 4H), 1.27 (s, 9H).

LCMS 20-70% MeCN: 0.1% formic acid/water; short acid methods, C18-CSA, 1.03 min m/z (+ve) 268.1/270.1 (loss of boc+H).

(R)—N-Boc-norketamine-6-trimethylsilyl enol ether (48)

The trimethylsilyl enol ether of Boc protected R-norketamine was achieved with 99% yield by treating with strong base (lithium diisopropylamide (LDA)) in THF at −78° C., taking care to remove trace moisture from the reagents to avoid stalling the reaction.

(2R,6R)—N-Boc-6-hydroxynorketamine (49)

Alpha hydroxylation of the trimethyl silyl enol ether of R-norketamine was achieved with 92% yield using AD-mix alpha under Sharpless dihydroxylation conditions for 16 hours, with hydroxylation occurring exclusively syn to the Boc protected amine group. The same product was obtained using AD-mix beta under Sharpless conditions, with 93% yield.

Compound 49 was also obtained directly from Boc protected R-norketamine in a one pot, two step reaction by treating with LDA in THF at −78° C. for 1.5 hours, followed by addition of Davies oxaziridine and allowing the temperature to rise from −78° C. to room temperature over 16 hours.

1H-NMR (301 MHz, CHLOROFORM-D) δ 7.81 (d, J=6.2 Hz, 1H), 7.28-7.39 (m, 3H), 6.60 (s, 1H), 4.14 (dd, J=11.4, 6.9 Hz, 1H), 3.89 (d, J=11.4 Hz, 1H), 3.33 (s, 1H), 2.34-2.42 (m, 1H), 1.44-1.77 (m, 7H), 1.31 (s, 9H) LCMS (dihydroxylation route) Short acid 2-95% MeCN: 0.1% formic acid/H2O; 0.79 min Rt=product [M-Boc+H]+; 0.87=Product+TMS (so 6-TMSO-HNK) minus tert-butyl Data is indicative that the TMS group undergoes in situ transfer to the 6-OH as the hemi-silyl-acetal, and then breaks down to form the ketone.

2R,6R-hydroxynorketamine (27)

Compound 49 was Boc-deprotected with 88% yield by treating with HCl in cyclopentyl methyl ether.

1H-NMR (301 MHz, METHANOL-D3) δ 7.86-7.88 (m, 1H), 7.53-7.61 (m, 3H), 4.29 (dd, J=11.5, 6.7 Hz, 1H), 3.18-3.25 (m, 1H), 2.28-2.33 (m, 1H), 1.55-1.96 (m, 4H).

LCMS 2-50% MeCN: 10 mM ammonium carbonate @ PH10, C18-XB; Rt 0.72 min m/z (+ve) 240.1/240.2 (M+H-freebase)

Example 2: Formation of Crystalline Forms of 2R,6R-hydroxynorketamine Salts

Methods of Analysis

X-Ray Powder Diffraction (XRPD)—Transmission

XRPD analysis was carried out on a PANalytical X'pert pro, scanning the samples between 3 and 35° 2θ. The material was gently ground to release any agglomerates and loaded onto a multi-well plate with Kapton or Mylar polymer film to support the sample. The multi-well plate was then placed into the diffractometer and analysed using Cu K radiation (α1 λ=1.54060 Å; α2=1.54443 Å; β=1.39225 Å; α1:α2 ratio=0.5) running in transmission mode (step size 0.0130° 2θ) using 40 kV/40 mA generator settings.

X-Ray Powder Diffraction (XRPD)—Reflectance

XRPD analysis was carried out on a Philips X'pert Pro Multipurpose Diffractometer using a spinning stage with autosampler, scanning the samples between 3 and 35° 2θ. The material was loaded onto a circular sample holder and flattened using a glass slide. The sample holder was then loaded into position on the autosampler cassette and analysed using Cu K radiation (α1 λ=1.54060 Å; α2=1.54443 Å; β=1.39225 Å; α1:α2 ratio=0.5) running in reflectance mode (step size 0.013° 2θ, time per step 59.67 s) using 40 kV/40 mA generator settings and fitted with a Ni Cu Kβ filter).

Polarised Light Microscopy (PLM)

The presence of crystallinity (birefringence) was determined using an Olympus BX50 polarising microscope, equipped with a Motic camera and image capture software (Motic Images Plus 2.0). All images were recorded using the 20× objective, unless otherwise stated.

Thermogravimetric Analysis (TGA)

Approximately 5 mg of material was weighed into an open aluminium pan and loaded into a simultaneous thermogravimetric/differential thermal analyser (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 cm$^3$/min.

Differential Scanning Calorimetry (DSC)

Approximately, 5 mg of material was weighed into an aluminium DSC pan and sealed non-hermetically with a pierced aluminium lid. The sample pan was then loaded into a Seiko DSC6200 (equipped with a cooler) cooled and held at 20° C. Once a stable heat-flow response was obtained, the sample and reference were heated to 180° C. at scan rate of 10° C./min and the resulting heat flow response monitored. Nitrogen was used as the purge gas, at a flow rate of 50 cm$^3$/min.

Infrared Spectroscopy (IR)

Infrared spectroscopy was carried out on a Bruker ALPHA P spectrometer. Sufficient material was placed onto the centre of the plate of the spectrometer and the spectra were obtained using the following parameters:

Resolution: 4 cm$^{-1}$; Background Scan Time: 16 scans; Sample Scan Time: 16 scans; Data Collection: 4000 to 400 cm$^{-1}$; Result Spectrum: Transmittance; Software: OPUS version 6

Nuclear Magnetic Resonance (NMR)

NMR experiments were performed on a Bruker AVIIIHD spectrometer equipped with a DCH cryoprobe operating at 500.12 MHz for protons. Experiments were performed in deuterated DMSO-d6 and each sample was prepared to ca. 10 mM concentration.

Dynamic Vapour Sorption (DVS)

Approximately, 10 mg of sample was placed into a mesh vapour sorption balance pan and loaded into a DVS-1 dynamic vapour sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

Approximately, 10-20 mg of sample was placed into a mesh vapour sorption balance pan and loaded into a DVS Intrinsic dynamic vapour sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

Gravimetric Vapour Sorption (GVS)

Approximately 10-20 mg of sample was placed into a mesh vapour sorption balance pan and loaded into an IGASorp Moisture Sorption Analyser balance by Hiden Analytical. The sample was subjected to a ramping profile from 40-90% relative humidity (RH) at 10% increments, maintaining the sample at each step until a stable weight had been achieved (98% step completion, minimum step length 30 minutes, maximum step length 60 minutes) at 25° C. After completion of the sorption cycle, the sample was dried using the same procedure to 0% RH, and finally taken back to the starting point of 40% RH. Two cycles were performed. The weight change during the sorption/desorption cycles were plotted, allowing for the hygroscopic nature of the sample to be determined.

Variable Humidity X-Ray Powder Diffraction (VH-XRPD)

VH-XRPD analysis was carried out on a Philips X'Pert Pro Multipurpose diffractometer equipped with a humidity chamber. The samples were scanned between 4 and 35.99° 2θ using Cu K radiation (α1 λ=1.54060 Å; α2=1.54443 Å; β=1.39225 Å; α1:α2 ratio=0.5) running in Bragg-Brentano geometry (step size 0.008° 2θ) using 40 kV/40 mA generator settings. Measurements were performed at 40% RH, 80% RH, 10% RH, 0% RH. The temperature was raised to 60° C., 100° C. and 120° C. all at 40% RH.

High Performance Liquid Chromatography-Ultraviolet Detection (HPLC-UV)

Instrument: Agilent 1100/Dionex Ultimate 3000; Column: Ace Excel-3 C18-AR, 75 mm×4.6 mm 3 μm; Column Temperature: 40° C.; Autosampler Temperature: Ambient; UV wavelength: 210 nm; Injection Volume: 10; Flow Rate: 1 mL/min; Mobile Phase A: 10 mM Ammonium Formate pH8; Mobile Phase B: 10 mM Ammonium Formate pH8: Acetonitrile 20:80

| Gradient program: Time (minutes) | Solvent B [%] |
| --- | --- |
| 0 | 12 |
| 1 | 12 |
| 11 | 100 |
| 11.1 | 12 |
| 15 | 12 |

Mass Spectrometry

Instrument: LCQ Advantage Ion Trap MS; Sample concentration: 1 mg/ml, +ve ion mode by infusion; Source voltage (kV): 4.50; Source current (μA): 80.00; Sheath gas flow rate: 20; Aux/Sweep gas flow rate: 0; Capillary voltage (V): 8.0; Capillary temp (° C.): 200; Tube lens (V, Sp): 40; HPLC conditions as above.

2.0 Solvent Solubility 90 mg of 2R,6R-hydroxynorketamine free base was dissolved in 18 mL of dichloromethane. 1 mL aliquots of the solution were allowed to evaporate in a fume hood. PLM images of the white solid that remained in the vial in which the material had been dissolved were recorded.

A known volume aliquot (typically 5 volumes) of solvent was added to approximately 5 mg 2R,6R-hydroxynorketamine. Between each addition, the mixture was checked for dissolution and where no dissolution was apparent, the mixture was heated to ca. 40° C. and checked again. This procedure was continued until dissolution was observed or until 1 mL of solvent had been added. Any remaining solids were analysed by XRPD. Where the material had fully dissolved, the solution was left to evaporate and any resulting solids were analysed by XRPD.

2.1 $pK_a$ Analysis

The sample pKa was determined using the potentiometric (pH-metric) technique following attempts to determine $pK_a$ via UV spectroscopic techniques.

UV-metric: The sample was initially titrated in a fast-UV triple titration between pH 2.0-12.0 at concentrations of 31-19 μM, under aqueous conditions. No evidence of any sample ionisation within the investigated pH range was inferred from the spectroscopic data obtained, meaning that any ionisable groups were remote from chromophores. Therefore, the sample was analysed using the pH-metric method.

pH-metric: The sample was subsequently titrated using the potentiometric technique to determine the non-UV active $pK_a$s. A triple titration was carried out under methanol-water co-solvent conditions from pH 2.0-12.0 at concentrations of 0.9-0.6 mM (the methanol mixing ratio varied from 53.0 to 33.3% w/w). No precipitation of the sample from solution was observed so the $pK_a$ was determined from the potentiometric data collected, by Yasuda-Shedlovsky extrapolation of the individual results obtained. $pK_a$ of 2R,6R-hydroxynorketamine was calculated as 6.51+/−0.02.

Candidate counterions were selected based on $pK_a$ compatibility.

2.2 Crystallisation of 2R,6R-Hydroxynorketamine Free Base

Figure 2A:
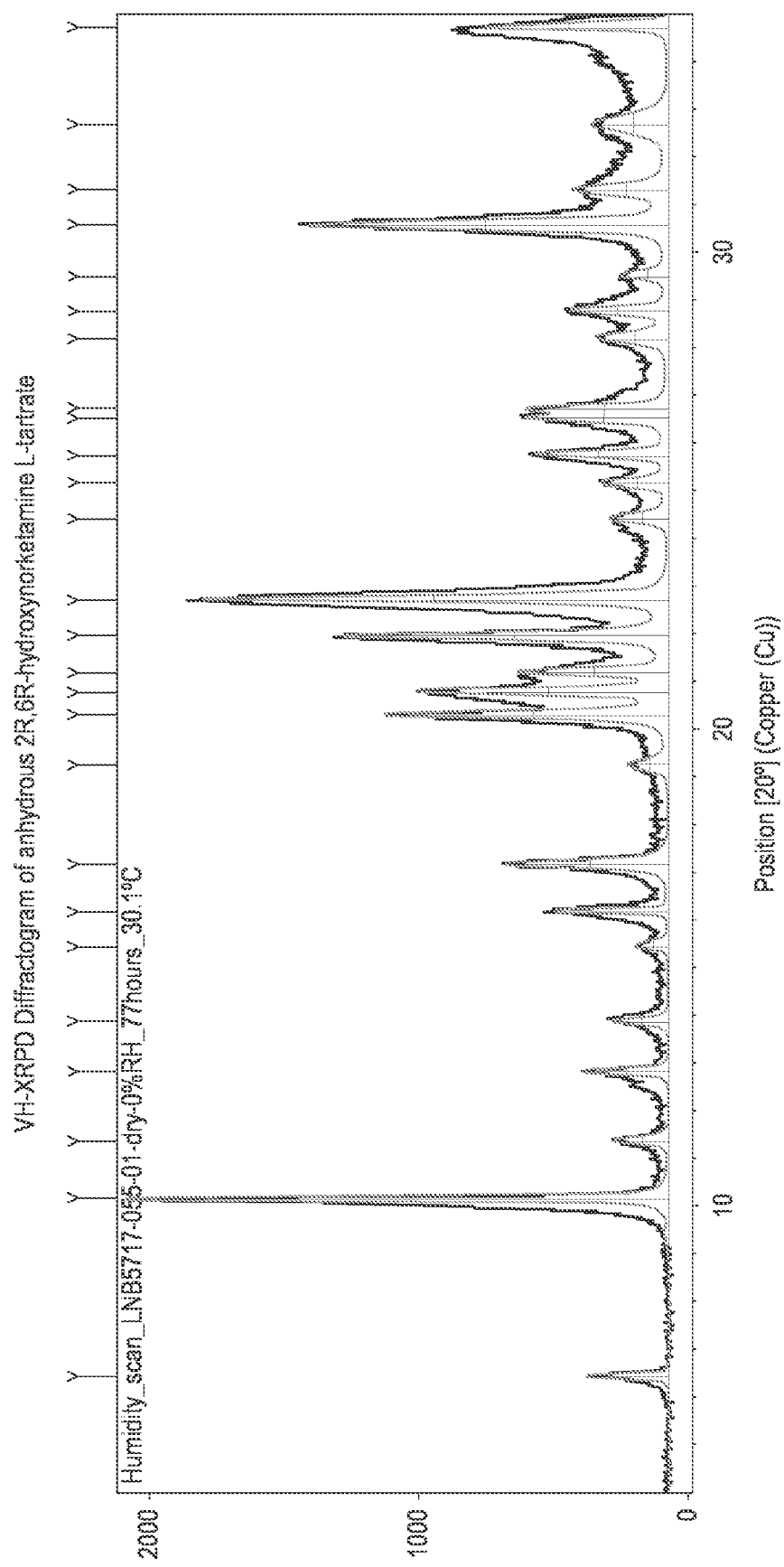
FIG. 2A to 2E: shows VH-XRPD diffractogram of 2R,6R-hydroxynorketamine crystalline salt forms
Figure 2B:
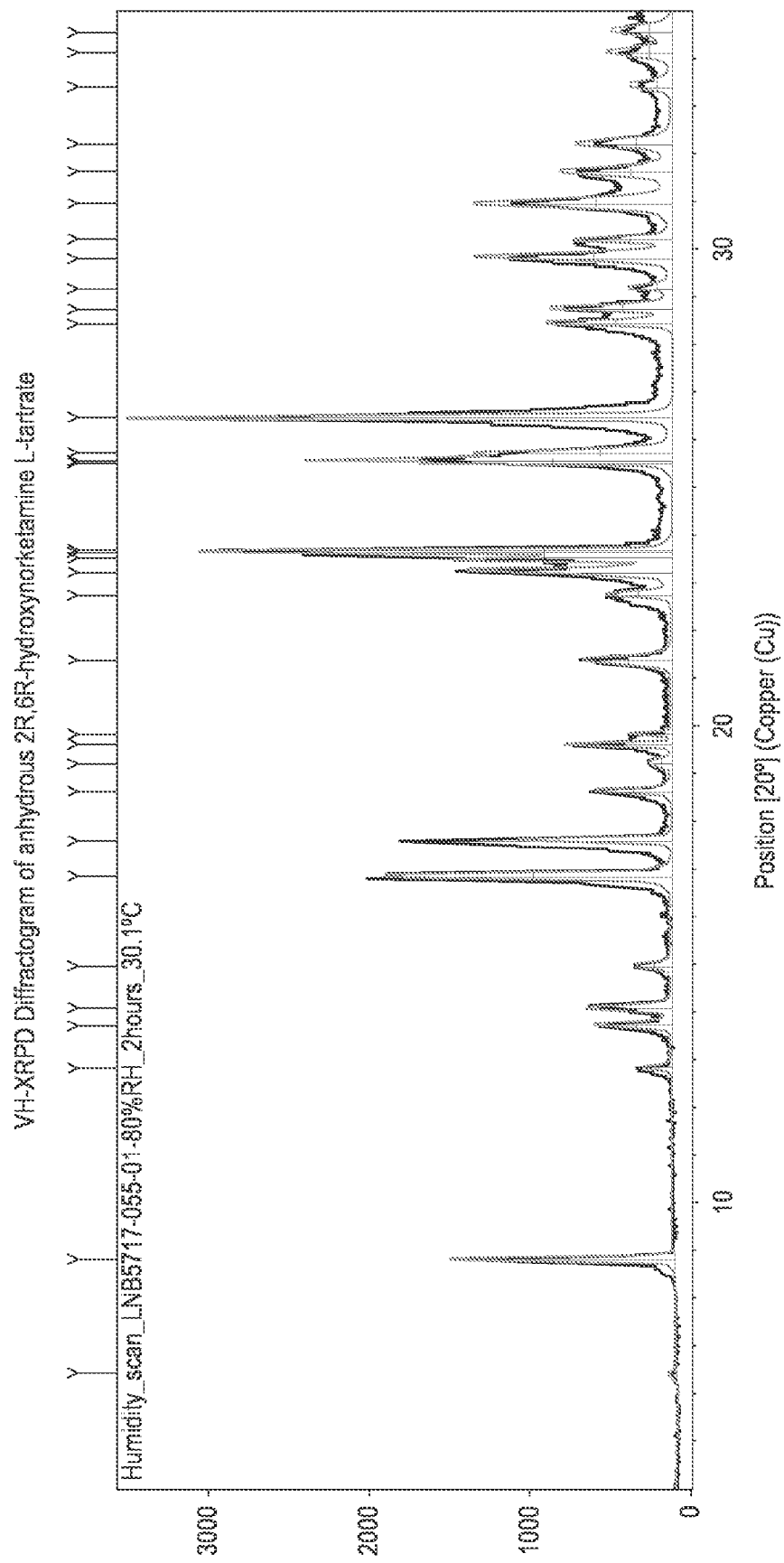
Figure 2C:
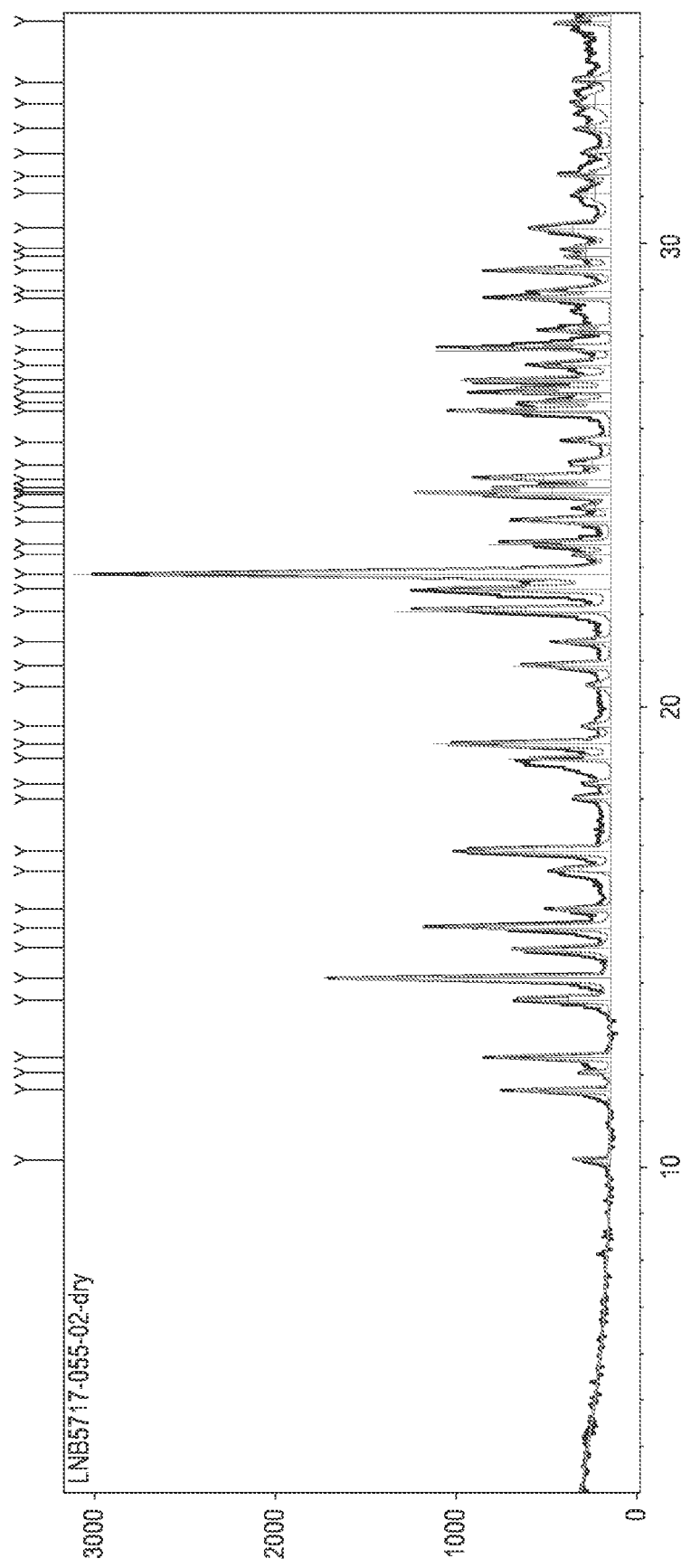
Figure 2D:
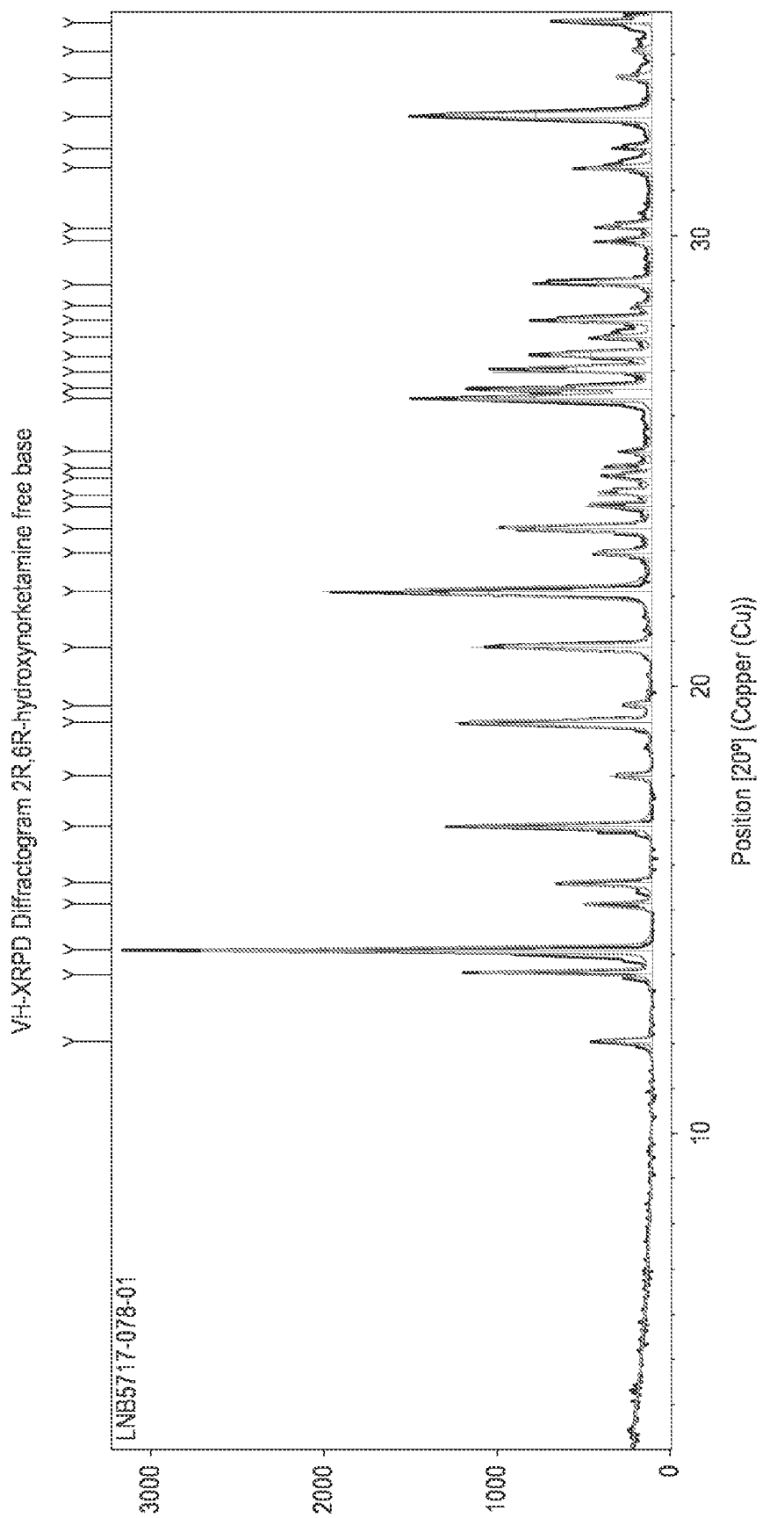
Figure 2E:
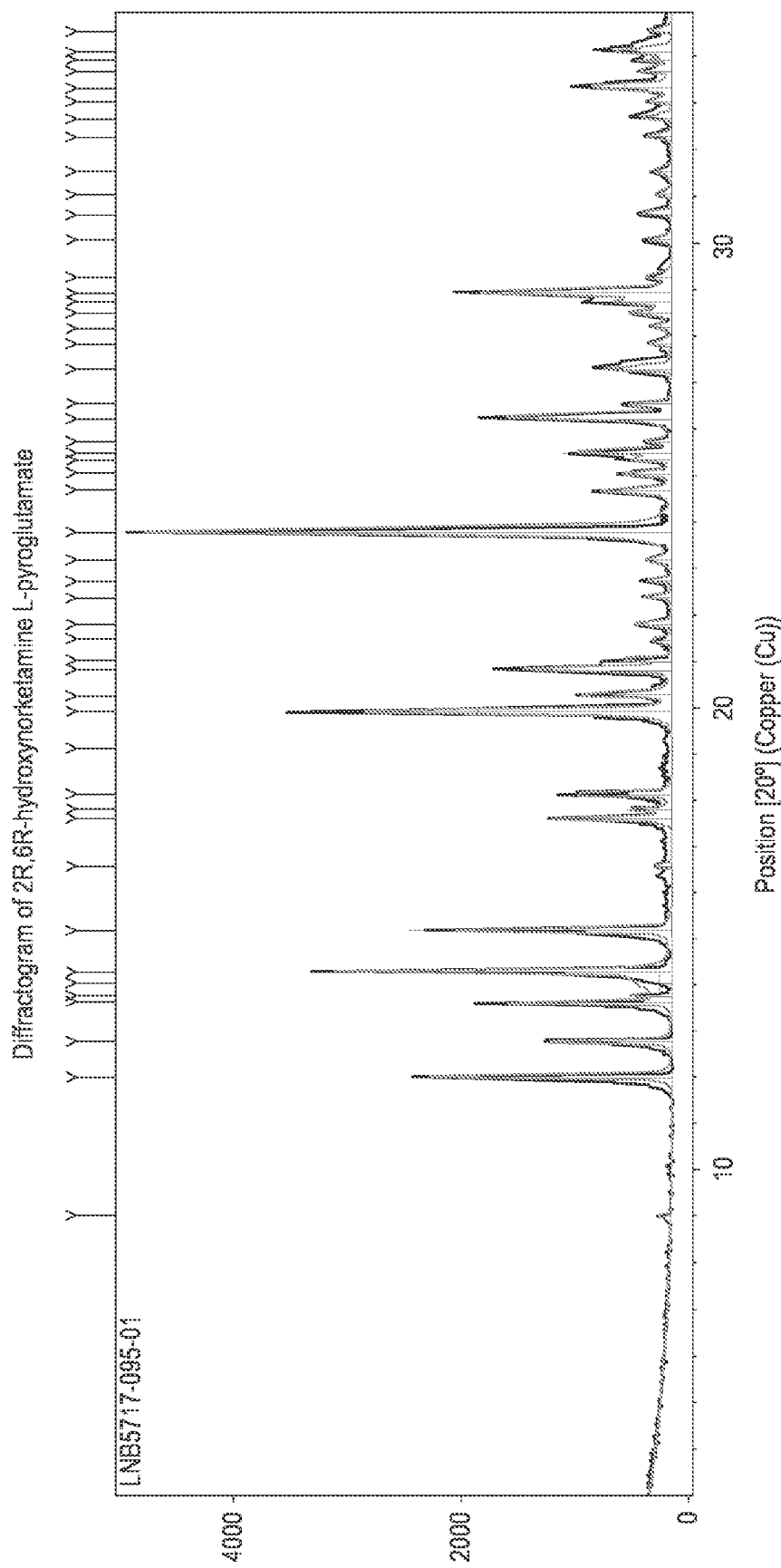
Figure 3:
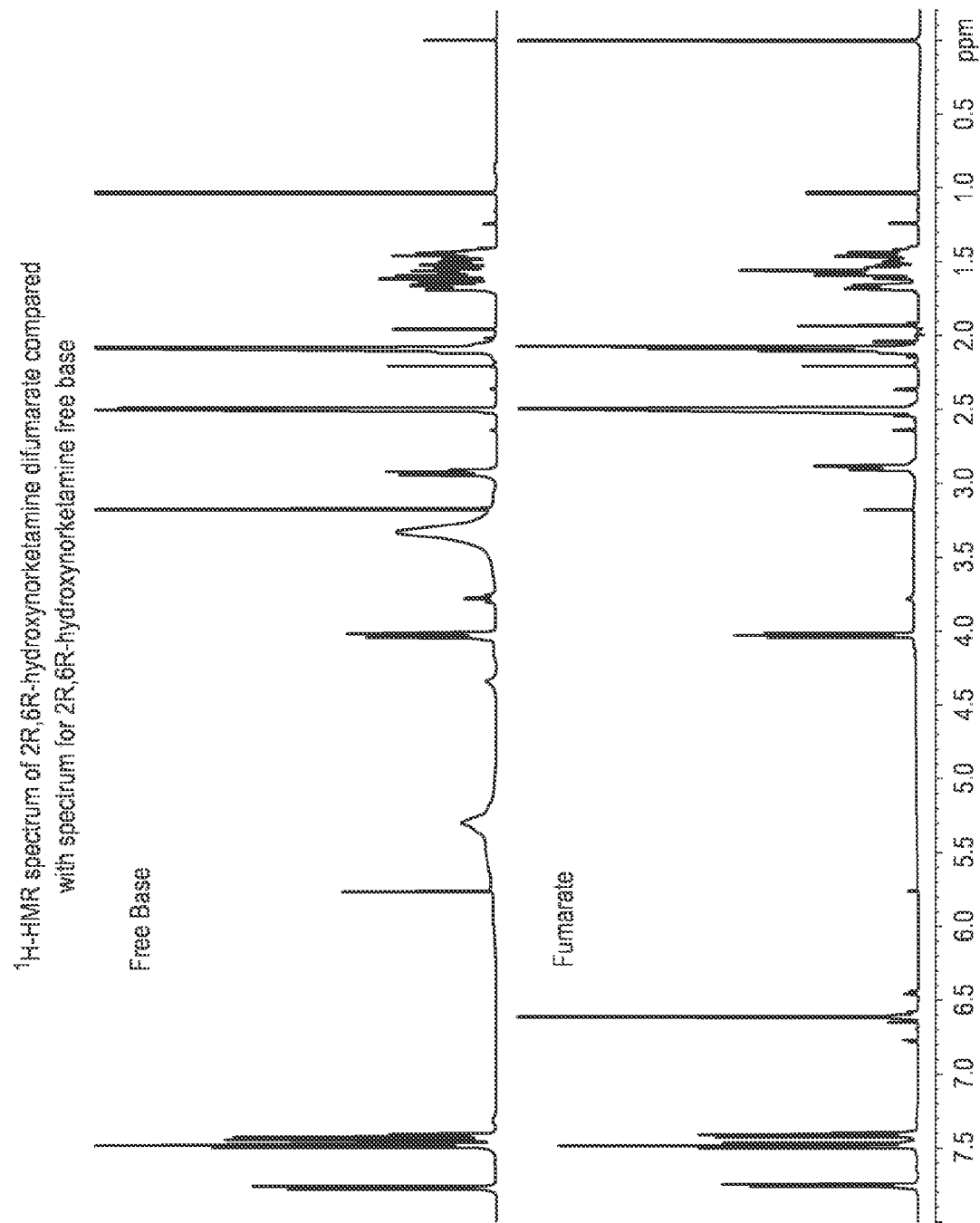
FIG. 3: $^1$H-NMR spectrum of 2R,6R-hydroxynorketamine difumarate compared with spectrum for 2R,6R-hydroxynorketamine free base

On addition of the 0.5 mL of acetonitrile to the 10 mg 2R,6R-hydroxynorketamine free base, the yellowish gum dissolved and white solids immediately crashed out, leaving a pale yellow clear solution. The solids were analysed by XRPD. The diffractogram is presented in FIG. 2D.

2.3 Crystallisation of 2R,6R-Hydroxynorketamine Hydrochloride 20 mg of 2R,6R-hydroxynorketamine was suspended in 100 μL each of acetone, acetonitrile, ethanol and tetrahydrofuran (THF). 87.6 μL of 1M hydrochloric acid stock solution prepared in water (1.05 equivalents) was added and the mixtures were then thermally cycled whilst being stirred for 48 hours according to the following program:

25° C. to 5° C. at 0.1° C./min; Hold at 5° C. for 1 hour; 5° C. to 25° C. at 0.1° C./min; Hold at 5° C. for 1 hour.

No solids were recovered post-thermal cycling so the solutions were uncapped and allowed to evaporate at ambient temperature and pressure.

No solids were recovered post-evaporation anti-solvent addition was carried out using t-butyl methyl ether (tBME) and the mixtures were matured for 16 hours. Further anti-solvent addition was then carried out and the mixtures were matured for 72 hours.

Clear solids of 2R,6R-hydroxynorketamine hydrochloride were recovered from acetone after treatment with anti-solvent. XRPD analysis was carried out on the solids. Significant preferred orientation was found, likely due to formation of needle-like crystals. The material was removed from the XRPD plate, ground and then re-analysed. Preferred orientation was again observed although in different peak positions.

2.4 Crystallisation of 2R,6R-hydroxynorketamine L-tartrate 20 mg of 2R,6R-hydroxynorketamine free base was suspended in 100 μL of organic solvent. 87.6 μL of 1M L-Tartaric acid stock solution prepared in water (1.05 equivalents) was added and the mixtures were then thermally cycled whilst being stirred for 48 hours according to the following program: 25° C. to 5° C. at 0.1° C./min; hold at 5° C. for 1 hour; 5° C. to 25° C. at 0.1° C./min; hold at 5° C. for 1 hour.

Solids were recovered from all solvent systems investigated. Post-thermal cycling, white solids were identified in acetone, acetonitrile and THF. Clear Solids were recovered from ethanol post-evaporation.

Subsequently, 2.5 mL of acetonitrile was added to 500 mg of 2R,6R-hydroxynorketamine free base. 2190 μL of 1M L-tartaric acid stock solution (1.05 equivalents) prepared in water was added and the mixture was thermally cycled for 72 hours according to the following program whilst being stirred: 25° C. to 5° C. at 0.1° C./min; hold at 5° C. for 1 hour; 5° C. to 25° C. at 0.1° C./min; hold at 5° C. for 1 hour. A small portion of solid was removed post thermal cycling for wet XRPD analysis to ensure that the correct material had been prepared. The remaining solids were isolated by Buchner filtration and dried under vacuum at ambient temperature for 3 hours.

2.5 Crystallisation of 2R,6R-Hydroxynorketamine Difumarate 20 mg of 2R,6R-hydroxynorketamine was suspended in 187.6 μL of organic solvent. 0.2 mg of fumaric acid (1.05 equivalents) was added neat and the mixtures were then thermally cycled whilst being stirred for 72 hours according to the following program: 25° C. to 5° C. at 0.1° C./min; hold at 5° C. for 1 hour; 5° C. to 25° C. at 0.1° C./min; hold at 5° C. for 1 hour.

White solids were recovered from all solvent systems investigated. Post-thermal cycling, white solids were identified in acetone, acetonitrile, ethanol and THF.

The $^1$H-NMR spectrum of the fumaric acid solid recovered from acetonitrile is presented in FIG. 41. The singlet at 6.6 ppm with an integral of 4.2 protons gives 2 equivalents of fumaric acid per API. The presence of 2 equivalents of fumaric acid suggests the presence of a salt co-crystal.

Subsequently, 2.5 mL of acetonitrile was added to 500 mg of 2R,6R-hydroxynorketamine. 496.3 mg of fumaric acid (2.05 equivalents) was added and the mixture was thermally cycled for 72 hours according to the following program whilst being stirred: 25° C. to 5° C. at 0.1° C./min; hold at 5° C. for 1 hour; 5° C. to 25° C. at 0.1° C./min; hold at 5° C. for 1 hour.

A small portion of solid was removed post thermal cycling for wet XRPD analysis to ensure that the correct material had been prepared. The remaining solids were isolated by Buchner filtration and dried under vacuum at ambient temperature for 3 hours.

2.6 Crystallisation of 2R,6R-Hydroxynorketamine L-Malate 20 mg of 2R,6R-hydroxynorketamine was suspended in 100 μL of organic solvent. 87.6 μL of 1M L-Malic acid stock solution prepared in water (1.05 equivalents) was added and the mixtures were then thermally cycled whilst being stirred for 72 hours according to the following program: 25° C. to 5° C. at 0.1° C./min; hold at 5° C. for 1 hour; 5° C. to 25° C. at 0.1° C./min; hold at 5° C. for 1 hour. No solids were recovered post-thermal cycling so the solutions were uncapped and allowed to evaporate at ambient temperature and pressure.

No solids were recovered post-evaporation so anti-solvent addition was carried out using tBME and the mixtures were matured for 16 hours. Further anti-solvent addition was carried out and the mixtures were matured for 72 hours. Clear solids were recovered from acetonitrile and ethanol following anti-solvent addition.

2.7 Crystallisation of 2R,6R-Hydroxynorketamine D-Malate 20 mg of 2R,6R-hydroxynorketamine was suspended in 100 μL of organic solvent. 87.6 μL of 1M D-Malic acid stock solution prepared in water (1.05 equivalents) was added and the mixtures were then thermally cycled whilst being stirred for 72 hours according to the following program: 25° C. to 5° C. at 0.1° C./min; hold at 5° C. for 1 hour; 5° C. to 25° C. at 0.1° C./min; hold at 5° C. for 1 hour. No solids were recovered post-thermal cycling so the solutions were uncapped and allowed to evaporate at ambient temperature and pressure.

No solids were recovered post-evaporation so anti-solvent addition was carried out using tBME and the mixtures were matured for 16 hours. Further anti-solvent addition was carried out and the mixtures were matured for 72 hours. Clear solids were recovered from acetone, acetonitrile, ethanol and THF following anti-solvent addition.

2.8 Crystallisation of 2R,6R-Hydroxynorketamine Citrate 20 mg of 2R,6R-hydroxynorketamine was suspended in 100 μL of organic solvent. 87.6 μL of 1M citric acid stock solution prepared in water (1.05 equivalents) was added and the mixtures were then thermally cycled whilst being stirred for 72 hours according to the following program: 25° C. to 5° C. at 0.1° C./min; hold at 5° C. for 1 hour; 5° C. to 25° C. at 0.1° C./min; hold at 5° C. for 1 hour. Solids were recovered from ethanol and THF post anti-solvent addition.

2.9 Crystallisation of 2R,6R-Hydroxynorketamine L-Pyroglutamate 20 mg of 2R,6R-hydroxynorketamine was suspended in 100 μL of organic solvent. 87.6 μL of 1M D,L-pyroglutamic acid stock solution prepared in water (1.05 equivalents) was added and the mixtures were then thermally cycled whilst being stirred for 72 hours according to the following program: 25° C. to 5° C. at 0.1° C./min; hold at 5° C. for 1 hour; 5° C. to 25° C. at 0.1° C./min; hold at 5° C. for 1 hour.

Crystalline material was recovered from acetone and acetonitrile post thermal cycling. The same XRPD pattern was found from THF post re-dissolving and maturation. Further analysis confirmed complete chiral resolution had occurred by recrystallization, and that the crystalline material obtained is 2R,6R-hydroxynorketamine L-pyroglutamate. Repetition of the above method with 2S,6S-hydroxynorketamine yields 2S,6S-hydroxynorketamine D-pyroglutamate.

2.10 Crystallisation of 2R,6R-Hydroxynorketamine Acetate 20 mg of 2R,6R-hydroxynorketamine was suspended in 100 μL of organic solvent. 87.6 μL of 1M acetic acid stock solution prepared in water (1.05 equivalents) was added and the mixtures were then thermally cycled whilst being stirred for 72 hours according to the following program: 25° C. to 5° C. at 0.1° C./min; hold at 5° C. for 1 hour; 5° C. to 25° C. at 0.1° C./min; hold at 5° C. for 1 hour.

No solids were recovered post-thermal cycling so the solutions were uncapped and allowed to evaporate at ambient temperature and pressure. No solids were recovered post-evaporation anti-solvent addition was carried out using tBME and the mixtures were matured for 16 hours. Further anti-solvent addition was carried out and the mixtures were matured for 72 hours. Clear solids were recovered from the acetic acid salt screen in ethanol post anti-solvent addition.

2.11 Crystallisation of 2R,6R-Hydroxynorketamine Tosylate 20 mg of 2R,6R-hydroxynorketamine was suspended in 100 μL of organic solvent. 87.6 μL of 1M acetic acid stock solution prepared in water (1.05 equivalents) was added and the mixtures were then thermally cycled whilst being stirred for 72 hours according to the following program: 25° C. to 5° C. at 0.1° C./min; hold at 5° C. for 1 hour; 5° C. to 25° C. at 0.1° C./min; hold at 5° C. for 1 hour.

Crystalline solids were recovered from acetone and THF post thermal-cycling. Acetonitrile and ethanol solutions were uncapped and allowed to evaporate at ambient temperature and pressure. Crystalline solids were recovered from acetonitrile post-evaporation.

2.12 Failure to Obtain Crystalline Salt Forms from Phosphoric Acid, Sulfuric Acid, Methane Sulfonic Acid, Benzene Sulfonic Acid, Benzoic Acid, D,L-Lactic Acid, and D,L-Mandelic Acid 20 mg of 2R,6R-hydroxynorketamine was suspended in 100 μL of organic solvent (each of acetone, acetonitrile, ethanol and THF). Crystallization was attempted in each solvent system with each of phosphoric acid, sulfuric acid, methane sulfuric acid, benzene sulfonic acid, benzoic acid, D,L-lactic acid, and D,L-mandelic acid. 87.6 µL of 1M acid stock solution prepared in water (1.05 equivalents) was added and the mixtures were then thermally cycled whilst being stirred for 48 hours according to the following program: 25° C. to 5° C. at 0.1° C./min; hold at 5° C. for 1 hour; 5° C. to 25° C. at 0.1° C./min; hold at 5° C. for 1 hour. For each acid no solids were recovered post-thermal cycling so the solutions were uncapped and allowed to evaporate at ambient temperature and pressure. For each acid, no solids were recovered post-evaporation so anti-solvent addition was carried out using tBME and the mixtures were matured for 16 hours. Further anti-solvent addition was carried out and the mixtures were matured for 72 hours. For each acid, no solids were recovered following anti-solvent addition.

Example 3: Thermometric Analysis of Crystal Forms of 2R,6R-Hydroxynorketamine

TG/DVA Analysis of 2R,6R-Hydroxynorketamine Hydrochloride

The TG/DTA Thermogram of the solids recovered from acetone is presented in FIG. 1A. TG/DTA shows that there is a sharp mass loss of 17.3 wt. % with an associated thermal event at 159° C. The sharp mass loss is attributed to loss of bound HCl which would be lost as a gas at that temperature, hence the sharp loss. The 17.3 wt. % loss calculates to 1 equivalent of HCl.

TG/DVA Analysis of 2R,6R-Hydroxynorketamine Difumarate

Figure 1B:
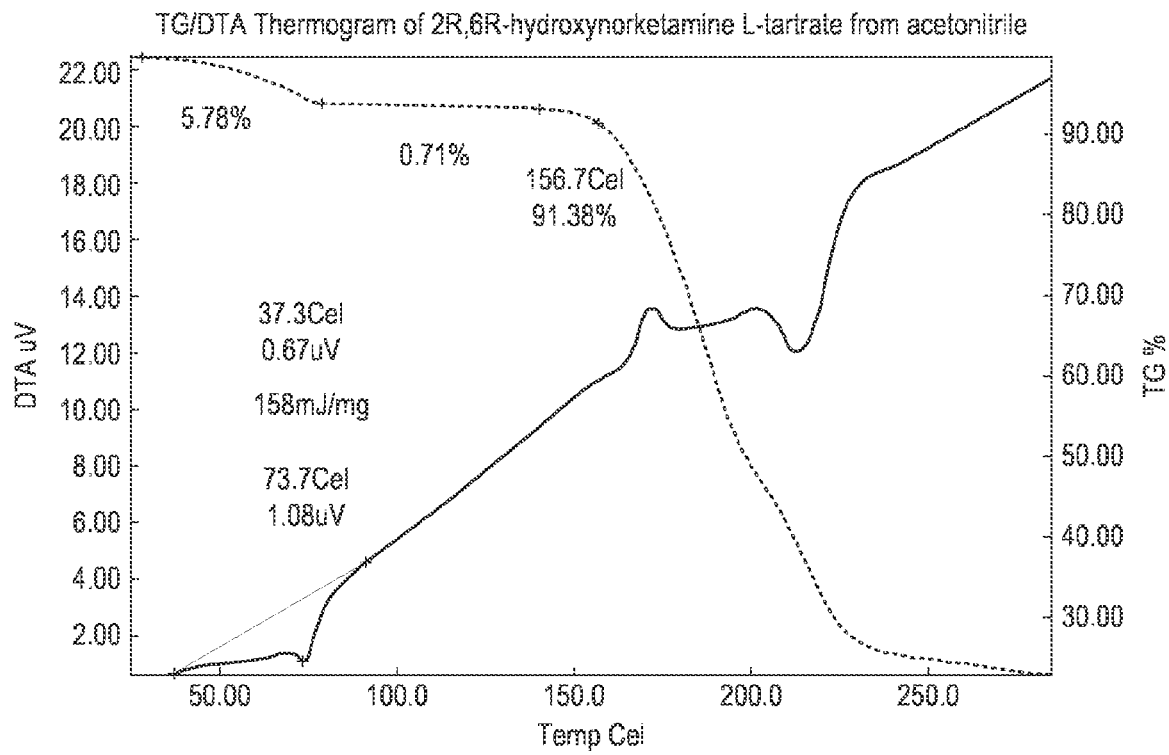

FIG. 1B presents the TG/DTA thermogram of the solid recovered from acetonitrile. The material degrades above 159° C. There were no thermal events in the DTA.

The 1H-NMR spectrum of the fumaric acid solid recovered from acetonitrile shows a singlet at 6.6 ppm with an integral of 4.2 protons gives 2 equivalents of fumaric acid per API. The presence of 2 equivalents of fumaric acid suggests the presence of a salt co-crystal.

TG/DVA Analysis of 2R,6R-Hydroxynorketamine L-Tartrate

Figure 1C:
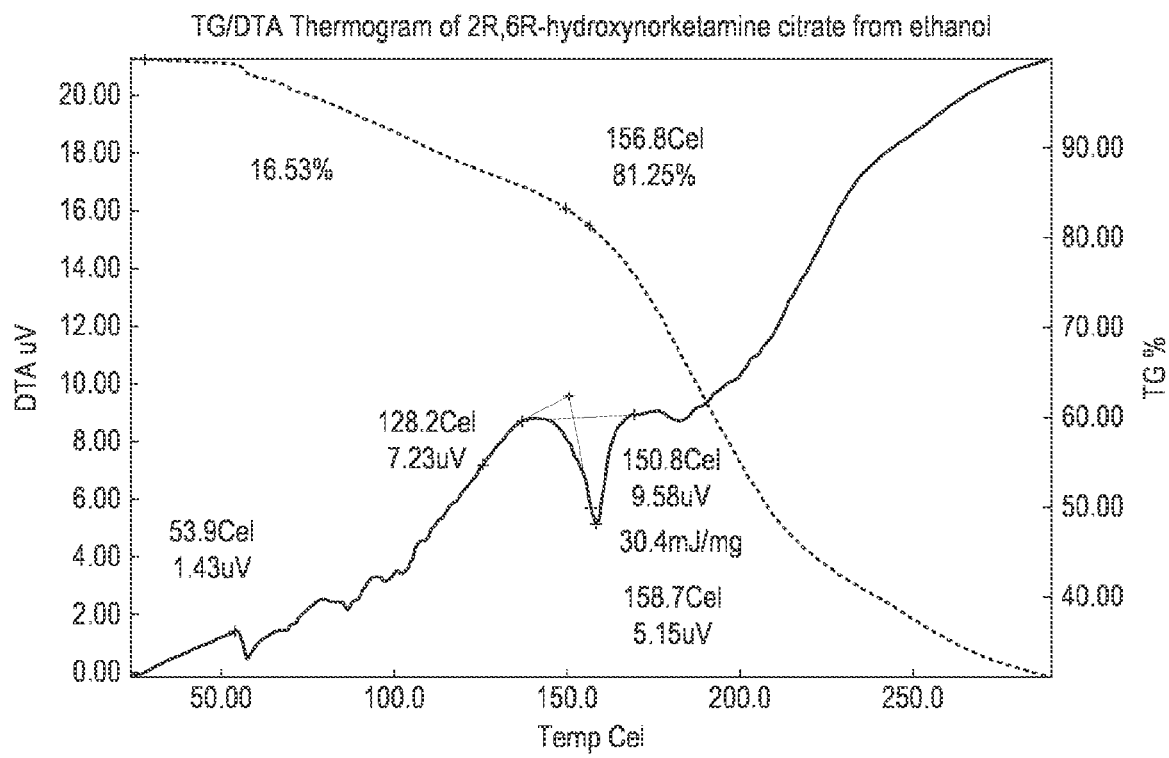

FIG. 1C presents the TG/DTA thermogram of the solid recovered from acetonitrile. A 5.8 wt. % loss is observed from the onset of heating with a related endotherm from the onset of heating with a peak at 74° C. The material degrades above 157° C.

1H-NMR analysis was carried out on the solids recovered from acetonitrile (FIG. 32). The singlet at 4.15 with an integral of 2.2 protons equals one equivalent of L-tartaric acid. This confirms that a L-tartrate salt has been made.

TG/DVA Analysis of 2R,6R-Hydroxynorketamine Citrate

Figure 1D:
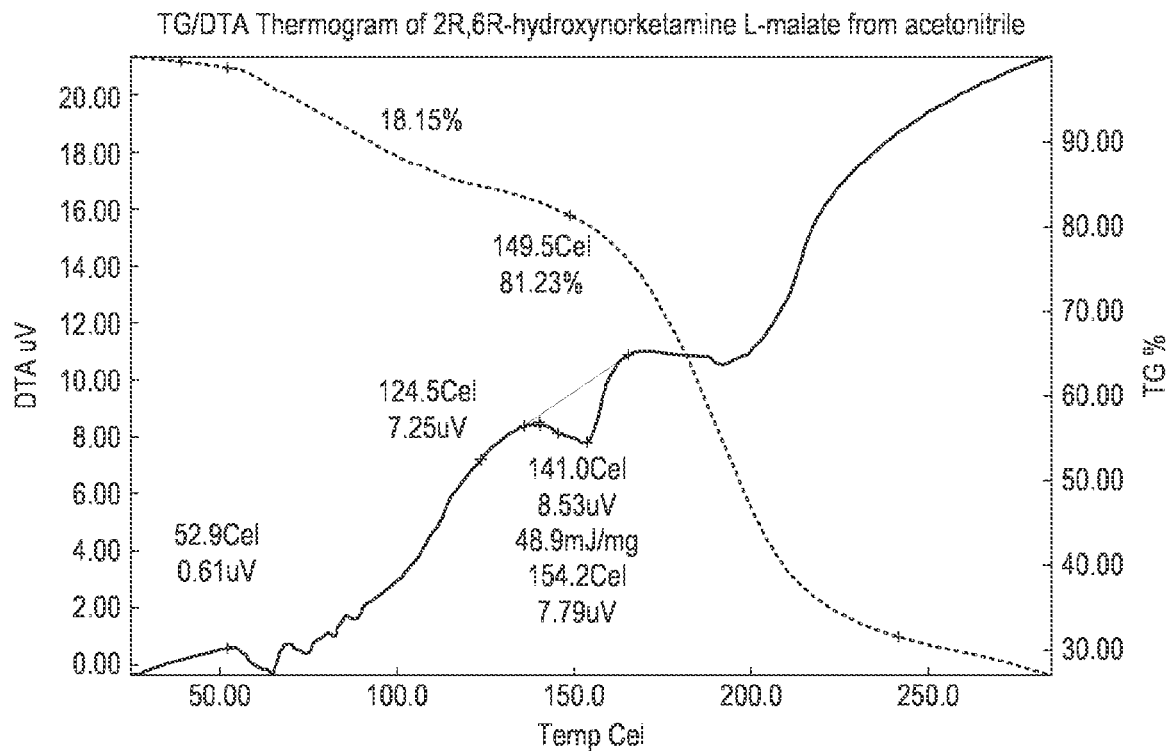

TG/DTA analysis was carried out on the solid recovered from ethanol. The thermogram is presented in FIG. 1D. There is a loss of 16.5 wt. % from the onset of heating with an associated endothermic event. There is an endotherm with onset 151° C. with a peak at 159° C. related to degradation of the material. The material degrades above 157° C.

TG/DVA Analysis of 2R,6R-Hydroxynorketamine L-Malate

Figure 1E:
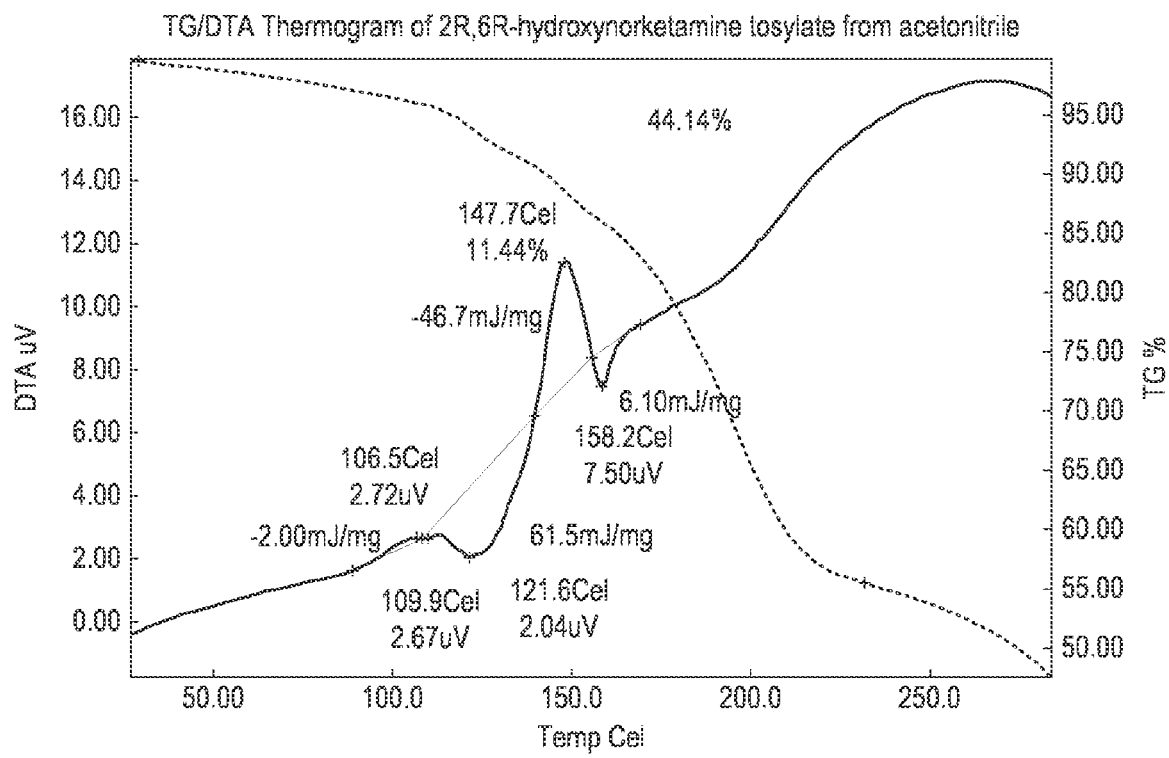

TG/DTA analysis was carried out on solids from acetonitrile, shown in FIG. 1E. There is a loss of 18 wt. % from the onset of heating with a related endotherm. The material degrades above 150° C.

TG/DVA Analysis of 2R,6R-Hydroxynorketamine Toluene Sulfonate

Figure 1F:
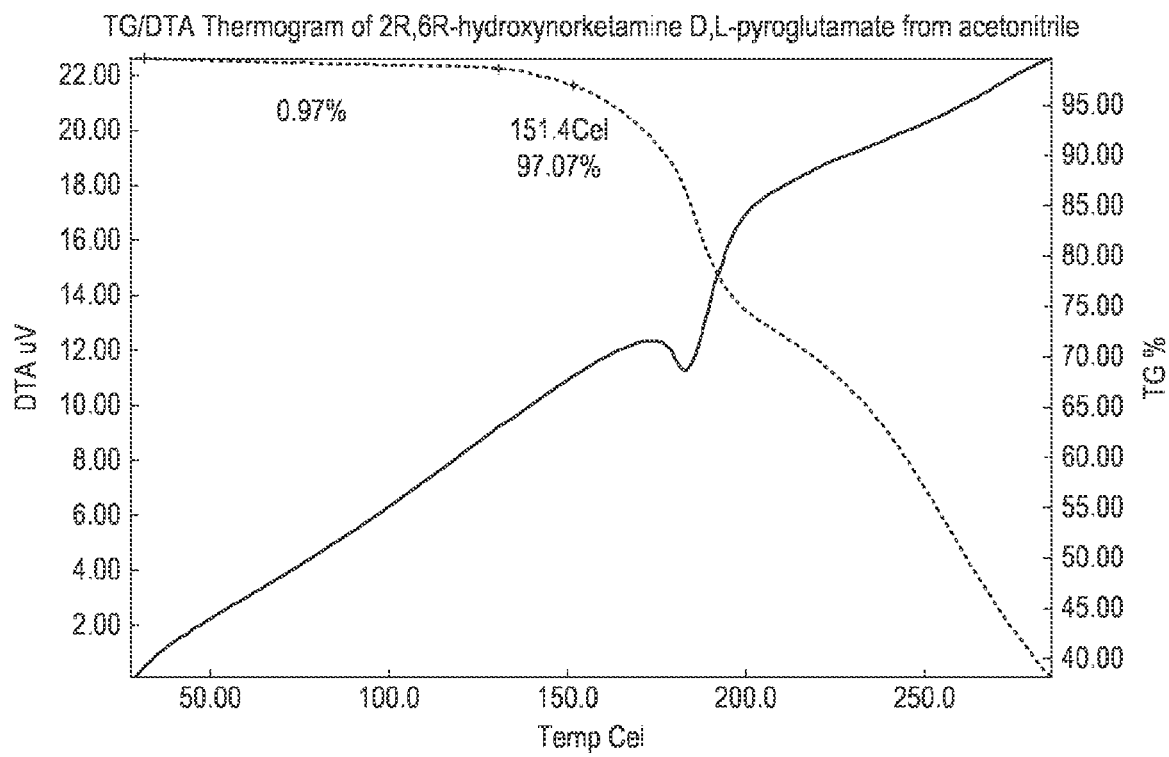

TG/DTA analysis was carried out on solids from acetonitrile, shown in FIG. 1F. Complex thermal events are observable.

TG/DVA Analysis of 2R,6R-Hydroxynorketamine D,L-Pyroglutamate

TG/DTA analysis was carried out on solids from acetonitrile, shown in FIG. 1F. There is a 1% mass loss from onset of heating. The material degrades above 159° C. There were no thermal events in the DVA.

Example 4: Solubility Analysis of 2R,6R-Hydroxynorketamine L-Pyroglutamate

A solubility assessment was carried out of 2R,6R-hydroxynorketamine L-pyroglutamate in various vehicles.

A solution of the received material in water for injection was submitted for analysis after being shaken at 400 rpm for 24 hours at 25° C. The solution was filtered through a pre-heated (at 25° C.) 0.22 µm PTFE filter into a HPLC vial. Samples were analysed after being diluted in deionised water to achieve a concentration of approximately 1000 µg/mL. HPLC method parameters used are provided in Table 1.

TABLE 1

| HPLC-UV Parameters | |
|---|---|
| System | Thermo Ultimate 3000 uHPLC with DAD |
| Analytical column | Ace Excel 3 C18 Ar 10 mm × 3 mm, particle size: 1.7 µm |
| Column temperature | 40° C. |
| Flow rate | 0.75 ml/min |
| Injection volume | 2.8 µl |
| Autosamper temperature | Ambient |

The method used is provided in Table 2. Analysis using this column showed that all peaks were sharp and no tailing was observed. Duplicate injections of standards gave consistent peak areas and no retention time drift or interfering peaks were observed.

TABLE 2

| Diluent | DI water | Column Used | 262 c |
|---|---|---|---|
| Mobile Phase | MPA: 100 mM Ammonium Formate pH 8.0:Water (10:90) MPB: 100 mM Ammonium Formate pH 8.0:Water:Acetonitrile (10:10:80) | Analytical Procedure | As per Table 1 |
| Detection Wavelength | 210 nm | Standard | 289/003-01 |
| Injection Volume (µL) | 2.8 | | |

Following the successful uHPLC solubility method assessment, solubility assessment of 2R,6R-hydroxynorketamine L-pyroglutamate in water for injection was conducted. A single replicant of the sample was prepared for the solubility assessment. Approximately 150 mg of 2R,6R-hydroxynorketamine L-pyroglutamate was weighed into a 2 mL HPLC vial prior to the addition of 1.0 mL of water for injection, forming a saturated solution. The sample was shaken at approximately 400 rpm for 24 hours at 25° C. After this the sample was hot filtered using pre-heated (at 25° C.) 0.22 µm PTFE syringe filters into a pre-heated HPLC vial. The samples were immediately analysed using the uHPLC method outlined above with analysis being performed on the samples diluted and undiluted for each of the major peaks observed. Analysis confirmed that 2R,6R-hydroxynorketamine L-pyroglutamate has a saturated solubility of 64 mg/mL in water for injection at 25° C., demonstrating significantly superior aqueous solubility over known crystal forms of 2R,6R-hydroxynorketamine hydrochloride (25 mg/mL).

This method was repeated to determine solubility of 2R,6R-hydroxynorketamine L-pyroglutamate in 0.9% saline. HPLC-UV parameters and methods were the same as described above. Analysis confirmed that 2R,6R-hydroxynorketamine L-pyroglutamate has a saturated solubility of 87 mg/mL in 0.9% saline at 25° C.

The invention claimed is:

1. An acid addition salt 2R,6R-hydroxynorketamine L-pyroglutamate having an X-ray powder diffraction pattern comprising a characteristic peak expressed in degrees 2-theta at position 14.3 further comprising characteristic peaks at positions 19.9 and 23.8 and further comprising characteristic peaks at positions 12.0, 13.6, 15.2, 20.8, 26.2, and 28.9.

2. The acid addition salt of claim 1 further comprising characteristic peaks expressed in degrees 2-theta at positions 12.8, 17.6, 18.1, and 25.5.

3. The acid addition salt of claim 2 further comprising characteristic peaks expressed in degrees 2-theta at positions 13.8, 14.1, 17.8, 20.3, 21.0, 21.8, 22.7, 24.6, 25.0, 25.3, 27.3, 28.5, 28.7, 30.6, 32.3, 32.7, 33.3, 33.9, and 34.1.

4. The acid addition salt of claim 2 further comprising characteristic peaks expressed in degrees 2-theta at positions 9.0, 16.6, 21.4, 22.4, 23.1, 25.7, 26.5, 27.8, 28.2, 29.3, 30.1, 31.1, 31.5, 33.1, 33.7, and 34.6.

* * * * *